United States Patent
Cook

(10) Patent No.: US 6,852,333 B1
(45) Date of Patent: Feb. 8, 2005

(54) AGENTS AND METHODS FOR PROMOTING PRODUCTION GAINS IN ANIMALS

(75) Inventor: Christian John Cook, Hamilton (NZ)

(73) Assignee: The Horticulture and Food Research Institute of New Zealand Limited, Palmerston North (NZ)

( * ) Notice: Subject to any disclaimer, the term of this patent is extended or adjusted under 35 U.S.C. 154(b) by 0 days.

(21) Appl. No.: 09/936,291

(22) PCT Filed: Mar. 13, 2000

(86) PCT No.: PCT/NZ00/00026
§ 371 (c)(1),
(2), (4) Date: Jan. 8, 2002

(87) PCT Pub. No.: WO00/54766
PCT Pub. Date: Sep. 21, 2000

(30) Foreign Application Priority Data

Mar. 12, 1999 (NZ) .............................................. 334627

(51) Int. Cl.[7] .......................... A23K 1/100; A61K 31/44
(52) U.S. Cl. ....................... 424/442; 424/408; 424/438; 514/9; 514/171; 514/355; 514/461; 514/561; 514/564
(58) Field of Search ................................ 424/617, 244; 574/561, 171, 355, 385, 396, 9–11, 564, 461

(56) References Cited

U.S. PATENT DOCUMENTS

| | | | | |
|---|---|---|---|---|
| 3,755,286 A | * | 8/1973 | Riniker et al. ............ | 260/112.5 |
| 4,871,550 A | | 10/1989 | Millman | |
| 5,643,954 A | | 7/1997 | Komissarova ............... | 514/561 |
| 5,728,675 A | * | 3/1998 | Schaefer et al. ................ | 514/2 |
| 5,937,790 A | * | 8/1999 | Ito et al. ...................... | 119/174 |
| 6,410,685 B1 | * | 6/2002 | Masuyama et al. .......... | 530/331 |

FOREIGN PATENT DOCUMENTS

| | | |
|---|---|---|
| AU | 30122/99 | 10/1999 |
| WO | WO82/00411 | 2/1982 |
| WO | 95 30418 | * 11/1995 |

OTHER PUBLICATIONS

JAVMA 202 #6 Dagy et al Case of Metyrapone —pp. 956–960 Mar. 93.*
Williams et al., "Enhancement of in vitro binding and some pharmacological properties of diazepam by a novel anthelmintic agent", Avermectin Bla, Eur. J. Pharmacol., vol. 56, pp. 273–276, XP002274490.
Ammendola et al., "Enhancement of some pharmacological properties of diazepam and pentobarbital by avermectin bla", Res. Comm in Psychology Psychiatry and Behavior, vol. 17, No. 3, 1992, pp. 133–146, XP009028073.
Kyriakis et al., "Thin sow syndrome. The effect of amperozide", Br. Vet. J., vol. 146, 1990; pp. 463–367, XP009028077.
Lanusse et al., "Enhancement of the plasma concentration of albendazole sulphoxide in sheep following coadministration of parenteral netobimin and liver oxidase inhibitors", Res. In Vet Sci., vol. 51, 1991, pp. 306–312, XP009028071.
Wang Shuwen: "Analgesics suitable for tumour treatment", Database WPI, Derwent Publications Ltd., Class B05, AN 2002–395184, XP002274491 3 '98.

* cited by examiner

Primary Examiner—Neil S. Levy
(74) Attorney, Agent, or Firm—Jacobson Holman PLLC

(57) ABSTRACT

The invention relates to compositions and methods for promoting production gains in animals, and of enhancing the efficacy of therapeutic agents. The gains are achieved through reduction in stress, including through the use of antistress agents. Compositions comprising therapeutic agents such as anthelmintics, and antistress agents are provided.

10 Claims, 14 Drawing Sheets

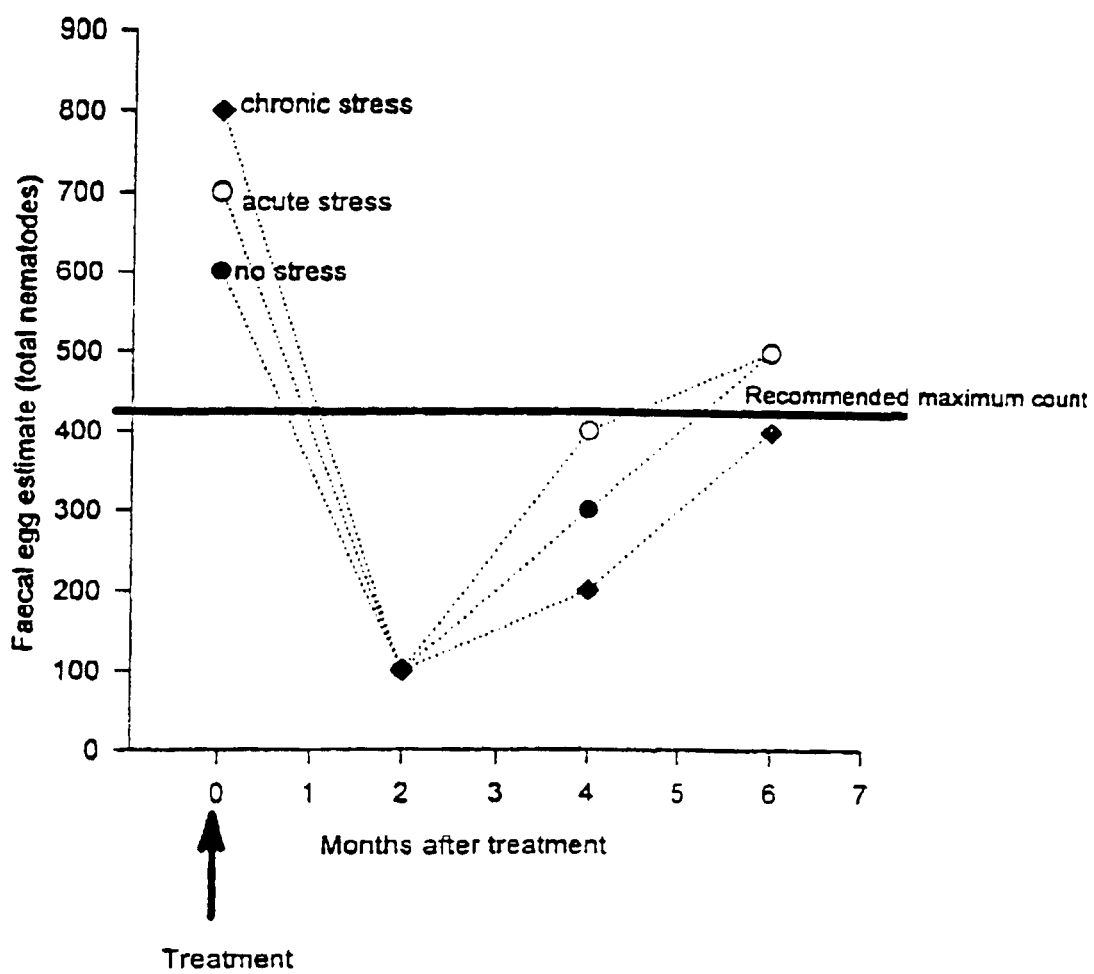

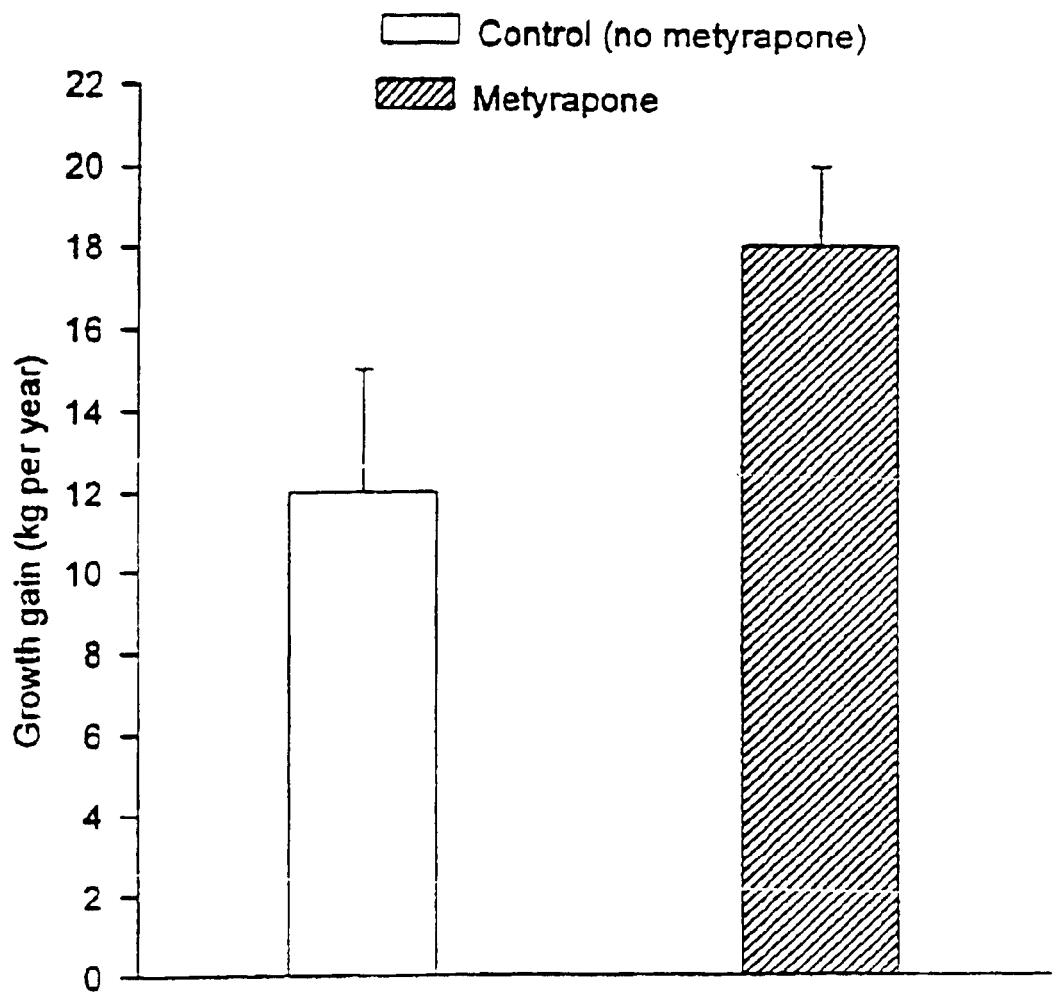

AGENTS AND METHODS FOR PROMOTING PRODUCTION GAINS IN ANIMALS

This is a nationalization of PCT/NZ00/99926 filed Mar. 13, 2000 and published in English.

FIELD OF THE INVENTION

This invention relates to methods and compositions for promoting production gains in animals and for enhancing efficacy of therapeutic agents.

BACKGROUND TO THE INVENTION

Animals are susceptible to both external and internal parasitic infection and disease. This is especially true in an agricultural environment where a high concentration of animals means that infection and reinfection can easily occur. Parasitic and disease loads on livestock are known to be responsible for a number of conditions such as poor growth, anaemia, scouring, indigestion, poor feed conversion, depression and premature death. These conditions hamper meat production and quality and have a detrimental economic impact on both the farmers and the industry in general.

In order to address this problem, therapeutic agents including vaccines, antibiotics, anthelmintics (also known as anthelmintics) and other anti-pathogenic agents have been used to control disease and the numbers of parasites in and on livestock. Therapeutic agents come in a number of forms, including drenches, pour-ons, wipe-ons, injectables, oral dosages or slow release compositions and are used to prevent, control or eliminate internal and external parasites and disease. Therapeutic agents and especially vaccines, antibiotics and anthelmintics are now well recognised as essential to healthy livestock growth.

However, therapeutic agents have disadvantages in that targeted organisms have been found to be developing resistance. One method used to tackle the increase in resistance has been to increase the number of doses and amounts of the agents administered to livestock.

It has also been shown that increasing agent use can, in and of itself, cause further resistance to the agents to develop.

As a result of increased agent usage, the costs of achieving the same disease or parasitic control per head of livestock escalate because of both an increase in labour and an increase in the amount of agent needed. A further problem encountered with more frequent use of some therapeutic agents is the build up of chemical residue within livestock, making the meat worth less and, in some cases, not fit for human consumption. Animals also suffer an increase in handling stress due to the need for increased handling to administer the agents more frequently.

It is also known in the art that handling stress is a contributory factor in livestock weight loss. This, in turn means that livestock use more pasture for less of an economic return. This problem has been found to be particularly acute in animals which have a propensity to be easily stressed.

Clearly, many of these disadvantages could be addressed if animal stress levels could be reduced and the efficacy of therapeutic agents administered could be increased.

U.S. Pat. No. 4,046,890 discloses a pharmacologically active group of benzodiazepine derivatives said to exhibit anthelmintic, anticonvulsant, sedative, and muscle relaxant activity. There is no suggestion that this multiplicity of properties is particularly advantageous, that anthelmintic effectiveness is superior to that of other anthelmintics, nor any suggestion that production gains were achieved using these compounds.

Nutritional supplements have been proposed for use in reducing the effects of stress on animals. Examples of such supplements are described in U.S. Pat. Nos. 5,505,968 and 4,600,586. U.S. Pat. No. 5,505,968 discloses a supplement comprising a combination of tryptophan, electrolytes, and amino acids. By improving animal nutrition the effects of stress on meat quality degradation, and loss in liveweight are said to be reduced. The composition does not treat stress per se. There is no suggestion to use the composition with therapeutics such as anthelmintics, nor a suggestion that production gains can be achieved with these supplements.

U.S. Pat. No. 4,600,586 similarly discloses a method for producing a feed supplement comprising primarily polyethylene glycol and molasses for use in reducing "lot adaptation stress". Minor ingredients are mixed to homogenicity with an effective amount of polyethylene glycol, then added to molasses and remaining polyethylene glycol. It is stated that if not mixed this way, that is, if merely admixed, then the composition is not effective to treat adaptation stress. Reduction in stress is achieved through increased metabolic utilisation of nutrients. The use of anxiolytics per se is not taught, the compositions are not suggested as being generically useful to treat stress. There is no suggestion that broad based production gains can be achieved using the nutritional supplement. There is no discussion of the combination of the supplement with anthelmintics or other therapeutic agents.

The applicants have now surprisingly found that antistress agents, and combinations thereof, when administered to an animal can generate a broad range of production gains in that animal. This property of antistress agents has not previously been recognised. Moreover, the applicants have also found that selected antistress agents, and combinations thereof, when administered to an animal can generate a broad range of production gains in that animal beyond what might be anticipated from reduction in stress alone.

Moreover, the applicants have also unexpectedly found that selected antistress agents when combined with therapeutic agents can increase the efficacy of the therapeutic agent in a synergistic manner.

An object of the present invention is to provide methods and agents for promoting production gains in animals or at least provide the public with a useful choice.

Other objects will be apparent from the statements and disclosure which follows.

SUMMARY OF THE INVENTION

A first aspect of the present invention provides a method for promoting production gain, in an animal, the method comprising administering at least one therapeutic agent to the animal and reducing the stress experienced by the animal.

In one embodiment, stress experienced by the animal is achieved by reducing physical causes of stress.

In an alternative embodiment, reduction in stress is achieved by administering an antistress agent to the animal.

Animal production gain is preferably a weight gain.

In accordance with a further aspect, the present invention provides a method for enhancing the efficacy of a therapeutic agent, the method comprising the co-administration of at least one therapeutic agent and at least one antistress agent.

In a further aspect, the present invention provides a therapeutic composition comprising at least one therapeutic agent and at least one antistress agent.

In one embodiment, the therapeutic composition is formulated as a slow-release composition.

Preferably, the therapeutic composition is an anthelmintic composition.

The invention extends to the use of antistress agents as adjuvants for therapeutic agents and compositions.

A further aspect of the present invention contemplated is the use of antistress agents as promoters of production gain in animals.

In a further aspect the invention provides a method of promoting production gain in an animal, the method comprising administering to said animal at least one antistress agent.

Desirably, the method comprises administering a composition of the invention.

In a preferred method of treatment, the animal is an animal infected with helminths and the therapeutic composition is an anthelmintic composition.

The invention also provides a second therapeutic composition comprising a therapeutic agent and a nitric oxide promoter.

BRIEF DESCRIPTION OF THE FIGURES

FIG. 4 is a line graph showing the effects of administration of metyrapone on acutely and chronically stressed animals.

FIG. 5 is a bar graph showing the effect on animal growth of metyrapone.

DETAILED DESCRIPTION OF THE INVENTION

Figure 1:
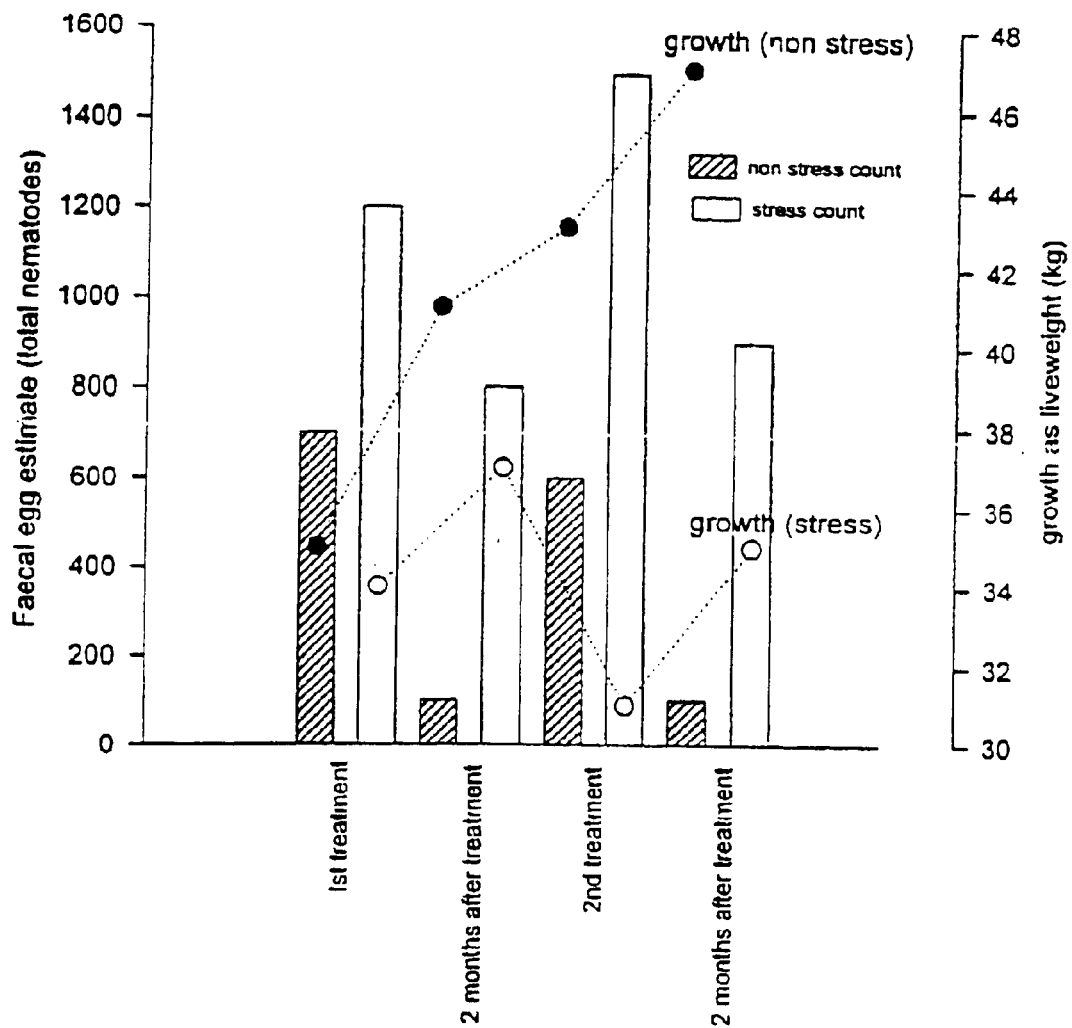
FIG. 1 is a bar graph with a superimposed line graph depicting the level of faecal egg estimates on the bar graph and animal growth on the line graph for chronically stressed animals and a control group.

As discussed above, the applicants have found that antistress agents, when administered to animals have unexpected effects in promoting a broad range of production gains in animals and increasing the efficacy of therapeutic agents. Selected antistress agents exhibit particularly surprising properties in promoting production gain and in increasing the efficacy of therapeutic agents. In an extension of this finding, the applicants have found that production gains may be surprisingly promoted by administering one or more therapeutic agents to an animal and reducing stress experienced by same.

In a first aspect, the present invention provides a method for promoting production gain, the method comprising administering at least one therapeutic agent to an animal and reducing stress experienced by the animal.

The term "production gain" as used herein is a broad term encompassing growth rates, increases in body weight, reproductive success, increase in birthweights, production against or recovery from trauma, efficiency of feed conversion, lean tissue mass and body fat reduction, or combinations thereof. These terms can be read alone or in combination in place of the term "production gain".

The term "reproductive success" as used herein refers to either or both of the number of animals achieving pregnancy, and the number of live births.

The phrase "protection against or recovery from trauma" as used herein refers to the ability to protect against, ameliorate the effects of, or aid recovery from trauma.

Animals susceptible to treatment according to the invention include humans and other animals. Other animals may encompass pets and livestock including cats, dogs, birds, pigs, sheep, fish, mink, deer, goats, cattle, horses, ducks, chickens and turkeys, but are not limited thereto. Best results are likely to be achieved with animals which are prone to high levels of stress.

Generally, the animals to be treated are sheep, deer, goats, cattle, chickens and pigs.

The term "therapeutic agent" as used herein refers broadly to agents useful in the treatment or prevention of disease or infestation in an animal or otherwise useful in promoting production gain such as animal growth, and well being. Included in the term are vaccines, antibiotics, anthelmintics, other anti-pathogenic agents, growth promoters, performance enhancers, vitamin, amino acid, and mineral supplements, or combinations of these, but are not limited thereto. The term "therapeutic composition" is to be similarly understood as broadly defined.

The term "performance enhancers" is used in the sense that it is employed in the pig and poultry industry to cover antibiotics and oligosaccharides that are primarily prophylactic or therapeutic against disease.

A very broad range of therapeutic agents are known in the art. Vaccines and antibiotics are described for example in *The Use of Antibiotics: A Clinical Review of Antibacterial, Antifungal and Antiviral Drugs,* A. Kucers, S. M. Crowe, M. L. Grayson, J. F. Hoy: 5th Edition Butterworth Heinemann 1997; and *Equine Drugs and Vaccines,* E. Kelton and T. Tobin, Breakthrough Pub. 1995; and *Vaccines for Veterinary Applications,* A. R. Peters (Ed.) 1993 all incorporated hereinby reference.

Anthelmintics are one preferred group of therapeutic agents for use in the present invention.

A broad range of anthelmintics suitable for use in the methods herein are also known in the art. A general reference text is Chemotherapy of Parasitic Disease; William Campbell, Plenum Publishing 1986 (incorporated herein by reference).

Suitable classes of anthelmintics which can be used include those active against cestodes, trematodes, nematodes and acanthocephala. The compounds may be selected from the group comprising simple heterocyclic compounds, benzimidazoles, imidazothiazoles, tetrahydropyrimidines, organophosphates, macrocyclic lactones, arsenicals and anticestodal drugs.

More preferably, suitable anthelmintic compounds are selected from the group comprising piperazine, diethylcarbamazine citrate, thiabendazole, fenbendazole, albendazole, oxfendazole, oxibendazole, febantel, tetramisole (levamisole, levamisole hydrochloride), pyrantel tartrate, pyrantel pamoate, morantel tartate, dichlorvos, milbemycin oxime, eprinomectin, moxidectin, N-butyl chloride, toluene, hygromycin B, sodium arsenamide sodium, melarsomnine, praziquantel, epsiprantel, clorsulon, triclabendazole, diazinon, benzimidazole, salicylamide, isoquinoline and cyromazine amongst others.

Preferred commercially available anthelmintics for use in the invention include Fasinex®, Soforen®, Endex®, Combinex®, Parifal®, Neocidol®, Acutak®, Dimpygal®, Nucidol®, Samicida®, Topclip®, Sentinel®, Vetrazin®, Avermectin®, Ivermectin® and Doramectin® but are not limited thereto. Combinations of two, three or more anthelmintics with the same or different anti-pest activity are also contemplated.

It will be appreciated by the reader that the amount of agent, delivery and timing varies in accordance with the compound employed, the animal species, bodyweight, age, type of parasite, degree of infestation and whether the treatment is therapeutic or prophylactic. Accordingly, in most cases dosing, and dosages will be carried out according to manufacturers instructions or as otherwise known in the art. For example, for anthelmintics where nematode counts in sheep exceed 600, dosing is generally recommended.

The therapeutic agents referenced above include drenches, pour-on formulations, injectables, oral dosage forms and slow release formulations, amongst others. It will therefore be appreciated that administration of the therapeutic agent at least orally, parenterally, topically and by injection is contemplated. Single and multiple dosing regimes are contemplated. Multiple dosing regimes may comprise administration of two or more agent doses to different sites on, or by different routes of administration to, an animal at the same time. Oral administration may also be achieved by supplying the agent in animal foodstuffs, or water.

In one embodiment, multiple dosing regimes may comprise administration of two or more doses of agents to different sites on an animal over a period of time covering hours, days, weeks or months.

In a preferred anthelmintic treatment regime, for larger animals, animals are dosed every two to four months by a combination of pour-on, injection and oral treatments.

For smaller animals or birds administration may be as a feed constituent on a daily, weekly, monthly, bimonthly or longer basis.

The applicant has also discovered that a combination of selected vitamins and long branched chain amino acids can exhibit a therapeutic effect. The combination comprises vitamin C with one or more amino acids selected from isoleucine, leucine, and valine, but preferably a combination of all three. The therapeutic effects achieved are an increase in effectiveness of therapeutics such as anthelmintics and increase in production gain such as growth in stressed animals. The combinations have also been shown to increase the effects of antistress agents such as metyrapone. The combinations therefor also exhibit antistress agent properties.

Each of the vitamin C and amino acids may be used in dose ranges of from 0.0001 g/kg to 1 g/kg of animal body weight.

Dosage rates for vitamin C when used in combination with antistress agents is generally between 0,005 to 0.5 g/kg, preferably 0.01 g/kg to 0.1 g/kg, and most preferably 0.1 g/kg.

Dosage rates for the amino acids when similarly used in combination with antistress agents is 0.0001 g/kg, and most preferably 0.001 g/kg to 0.005 g/kg and most preferably 0.005 g/kg.

The vitamin C and optimal amino acids may be administered separately, or together in a single composition. Dosage rates for the constituents when used separately can be readily calculated using protocols presented herein.

The present applicant has also found that the animal's state of stress, both acute and chronic, can contribute to the lasting efficacy of either a pour-on, oral or an injectable agent. Animals that have a high acute level of stress, at the time of application, or alternatively a low to high chronic stress load for some time prior to, or after, application show a lowered efficiency from the dosage and show a quicker re-infestation.

The stress undergone by the animal may be psychological stress or physical stress. Psychological stresses include restraint, handling and novelty stress. Physical stresses include hunger, thirst, fatigue, injury, trauma, surgery or thermal extreme stress. The stress may be also be chronic or acute.

The stress experienced by the animal may also be characterised as being of short duration or alternatively of long duration. In the case of short duration stress reduction, the stress reduction preferably takes place before the administration of the therapeutic agent, but can be after the administration of the agent. In the case of long duration stress reduction, the stress reduction is preferably of an order of at least the time between any agent administrations to the animal.

In one embodiment, stress reduction can be achieved by reducing physical causes of stress, preferably by way of reduced handling of the animals. This can be achieved by reducing intervention with the normal living patterns of the animal. It may include reducing animal (for example dog) and human interaction with the animals, limiting movements, shortening transport procedures and the like. However, physical stress reduction is not always practical.

Accordingly, in an alternative embodiment, stress reduction is achieved by administering at least one antistress agent to the animal.

The term "antistress agent" as used herein refers to compounds or compositions effective in reducing stress. This may be physiological or psychological stress or a combination thereof. Not included are agents which simply act as nutritional modifiers such as foodstuffs, for example, molasses and propylene glycol, or electrolyte combinations. Accordingly, the antistress agents used herein are not simply nutritional modifiers but are also physiological and/or psychological stress reducers per se. Any appropriate antistress compounds or compositions known in the art may be employed. The antistress agent is preferably long-acting, although short acting antistress agents are not excluded. In one embodiment, the antistress agent is formulated as a slow-release composition.

Suitable classes of antistress agents, including glucocorticoid inhibitors, corticotropin releasing hormone inhibitors, ACTH inhibitors, cholecystokinin inhibitors, benzodiazepines, gamma amino butyric acid potentiators, anti-glutaminergics and serotonergics amongst others. Preferred classes of antistress agents are pyridyl propanones including metyrapone, antiprogestins including mifepristone (RU 38486), and benzoylamino dipropylamino oxopentanoics including proglumide, and amino acids or peptides such as astressin which is a corticotropin releasing factor (CRF) antagonist. Selection of an antistress agent can be made according to broad criteria such as animal species, age, and types of stress. It is noted that antiprogestins are contradicted for use in pregnant or conceiving animals.

As discussed above, the applicant has also surprisingly found that vitamin C and specific amino acid combinations unexpectedly exhibit both therapeutic and antistress properties. Vitamin C alone and combinations with one or more of the amino acids valine, leucine and isoleucine are therefore also classed as anti-stress agents for the purposes of this invention.

More generally, preferred antistress agents include metyrapone, mifepristone (RU 38486), astressin, CRH 9-41, proglumide, diazepam, allopregnanolone, dextromethorphan, zimelidine, vitamin C in combination with valine, leucine and isoleucine, and paroxetine but are not limited thereto. Combinations of two, three or more antistress agents with the same or different activity are also contemplated for use herein. Combinations with vitamin C and one or more of the amino acids valine, leucine and isoleucine are also provided. A preferred combination for nonpregnant and nonconceiving animals includes metyrapone and mifepristone (RU 38486). For pregnant or conceiving animals proglumide or astressin and metyrapone is currently suggested.

Astressin is a strong anxiolytic agent and maybe of particular use in high stress situations such as injury, surgery or other trauma.

A particularly preferred antistress agent for use in the present invention is metyrapone. This compound acts to suppress some of the physiological and psychological stress responsiveness in an animal, including elevation of levels of glycocorticoid hormone cortisol.

Current results suggest that astressin, mifepristone, and vitamin C combinations can add to the production gain effects achieved with metyrapone. Vitamin C combinations increase the effects achieved. For combinations with metyrapone the effects of the other agents and combinations may also be increased once metyrapone is saturated.

Antistress agents may again be administered in a broad effective range. Appropriate dosage rates can be selected by the skilled reader according to known protocols for treating a variety of animals. Variation will occur based on the animal to be dosed, age, body weight and the like as discussed above. Dosages within the range of 0.000001 g/kg to 2 g/kg liveweight of total antistress agent whether a single agent or a combination is us ed, are feasible. Preferred ranges are 0.0005 to 1 g/kg, 0.001 to 0.1, and most preferably 0.01 to 0.1 g/kg. For metyrapone a preferred dosage range is 0.001 to 0.1 g/kg, preferably 0.01 g/kg liveweight.

Dosages within the range may not be suitable for all animals in given circumstances. Animals in different situations may respond differently. As illustrated in Example 8 higher or lower doses of the antistress agent may be appropriate for pigs under stress.

Figure 2:
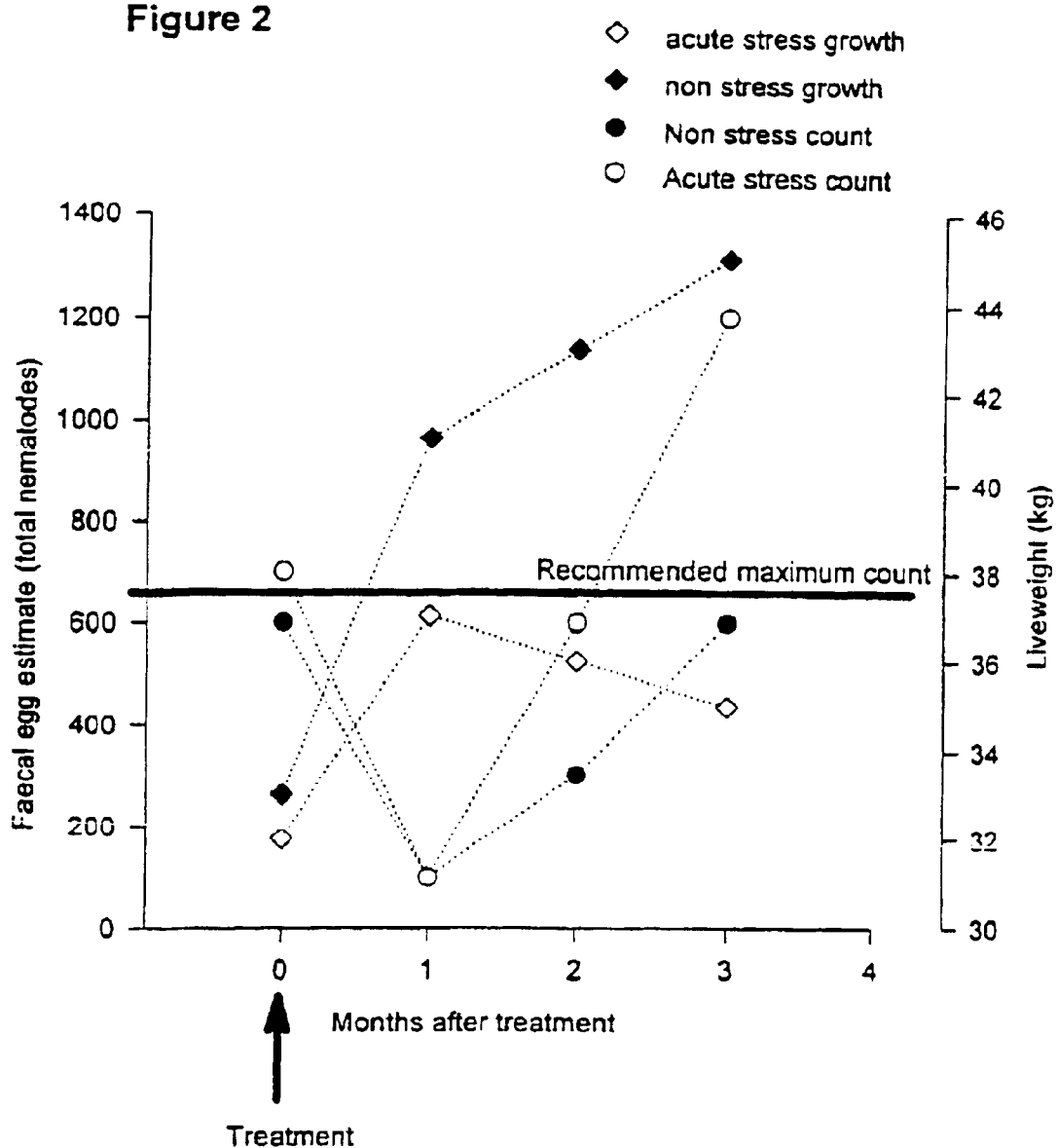
FIG. 2 is a line graph depicting the level of faecal egg estimates on the first Y axis and animal growth on the second Y axis line graph for acutely stressed animals and a control group.

Stressed animals that received this treatment with antistress agents showed approximately the same efficacy of anthelmintics as non-stressed animals and similar growth rates. This point is illustrated in accompanying FIGS. 2 to 4.

In a second aspect, the present invention provides a method for enhancing the efficacy of a therapeutic agent, the method comprising the co-administration of at least one therapeutic agent and at least one antistress agent to an animal. The antistress agent is preferably selected from the pyridyl propanone, progestin or peptide group of antistress agents, or is a vitamin C combination. Desirably, the agent is metyrapone.

Co-administration encompasses both concurrent and sequential administration. For sequential administration, it is not critical whether the therapeutic agent or antistress agent is administered first. Sequential administration may occur over a period of minutes, hours, or days. However, concurrent administration is preferred.

For concurrent administration, the therapeutic agent and antistress agent are preferably formulated in the same composition.

Accordingly, further aspect of the present invention relates to a therapeutic composition comprising at least one therapeutic agent and at least one antistress agent. The therapeutic and antistress agent may be selected from any of the therapeutics and antistress agents or combinations thereof referenced above or otherwise known in the art. The compositions are useful for promoting production gains in animals. Selected compositions may additionally exhibit synergistic properties. Foremost among these are compositions including at least one agent selected from vitamin C combinations and the progestin, peptide or pyridyl propanone group of antistress agents.

In a preferred composition, the therapeutic agent is an anthelmintic. In a particularly preferred composition, the anthelmintic is selected from Ivomec, Endex and levamisole and the antistress agent is metyrapone.

A further preferred composition also includes a non-vitamin C antistress agent and vitamin C, one or more of the amino acids selected from valine, leucine and isoleucine, or a combination thereof as discussed above. The addition of this vitamin and amino acids, or combination further enhances the effect of the antistress agent.

The amounts of therapeutic agent(s) and antistress agent(s) in the composition may vary within a broad range, so long as effectiveness is maintained. Antistress agent(s) will generally be present in individual or combined form between 0.0001 to 99.999% of the composition. Suitable concentrations can be calculated based on the weight/kg of liveweight dosage information given above. For best results across species tested to date, it is suggested that between 0.01 and 0.0001 g/kg be used together with 0.1–0.001 g/kg of vitamin C, and 0.005 g of each of valine, isoleucine and leucine.

As discussed above, the compositions of the invention can be formulated for oral, parenteral and topical administration or for injection.

To produce such formulations, the therapeutic compositions of the invention may further contain pharmaceutically or agriculturally acceptable carriers, diluents, excipients, disintegrators, stabilisers, and binding agents and such other materials as are known in the art and customarily employed in such formulations. The compositions may further comprise preservatives, antioxidants, colourants, feedstuffs, nutrients, vitamins, lubricants, salts, lipid membrane transfer facilitators, other therapeutic agents and nitric oxide promoters discussed later herein. This list is illustrative rather than exhaustive of the components of the composition. Suitable substances are well known in the art, for example in Pitha et al 1986; Amorphous water soluble derivatives of cyclodextrins: nontoxic enhancing excipients. J. Pharm Sci 74 (9) 987.

The applicant also hypothesised that the effectiveness of the composition could be further enhanced through the use of a lipid membrane transfer facilitator, to assist the transfer of the therapeutic and antistress agents across cell membranes. This has proved to be the case. Compositions further including a lipid membrane transfer facilitator are therefore contemplated. Facilitators know in the art include pyrolidones such as N-methylpyrolidone, and pyrimidines such as pyrrolopyrimidine, amongst others. Preferred facilitators are pyrrolopyrimidine and U-101033E (Also see Andreous P et al. *J. Neuro Science Res.*, 47: 650–654 and Hall E et al 1995 *Acta NeuroChir* 66: 107–113 incorporated herein by reference). The concentration of the facilitator may be from 0.0000001 to 10% of the antistress agent component, preferably 0.01 to 0.1%

Performance enhancers are a group of therapeutic agents including antibiotics and muccan oligosaccharides. They are of particular importance in the pig and poultry industry. An example of such an enhancer for use is Avilamycin at a concentration of between 0.01 to 0.5 g/kg, preferably 0.2 g/kg.

Bio-Mos (Altech Inc, Kentucky, USA) is an example of a mannan oligosaccharide. An appropriate range for the oligosaccharides is from 0.01 g/kg to 5 g/kg of liveweight, preferably 1 g/kg.

Solubilisers can be important components for solubility in aqueous solutions, and should be non-toxic. Many suitable solubilisers are known in the art. An example of a preferred solubiliser that may be used is 2-hydroxoypropyl-beta-cyclodextrin from 1 to 45% of the solution.

A typical composition for delivery could consist of 0.001% metyrapone, 0.01% vitamin C, 0.0005% each valine, isoleucine and leucine, 0.0001% pyrrolopyrimidine, 5% glucose, 0.1% sodium benzoate and the remainder up to a 1 L or 1 kg total coming from a carrier fluid or feed.

In one preferred embodiment, the composition is formulated as a slow-release composition, such as are known in the art. Slow release of the composition may conveniently be achieved through the use of boluses or time release capsules.

Examples of boluses contemplated by the invention are those as set out, for example in GB 2, 122,086, U.S. Pat. Nos. 3,535,419 and 5,720,972, which are incorporated herein by reference.

Using the methods and/or compositions of the invention, the applicants have also found that selected antistress agents especially those from the pyridyl propanone group when combined with therapeutic agents or compositions increase the efficacy of the therapeutic agent beyond what would be expected for the agents acting alone. Efficacy is usefully measured either in terms of increased effectiveness or duration of effectiveness of therapeutic agent. The route of action may vary. For example, in the case of vaccines, the antistress agent may act to increase the antibody titre and hence effectiveness.

The use of these treatments or compositions can therefore reduce the total number of therapeutic treatments needed in a year for effective results. A particular advantage here is that more time may be provided for residue clearance. Alternatively, if the number of treatments remains the same then a corresponding increase in effectiveness of the therapeutic agents should be seen. This means that the effective amount of the therapeutic agent required is reduced.

A still further benefit is reduction in stress at any stage in an animal's life, including in a pen prior to slaughter, where stress can reduce overall meat yield and quality.

Compositions and methods of the invention employing a therapeutic agent and an antistress agent all exhibit a significant benefit in promoting production gains, especially animal growth (e.g. weight gain), reproductive success and improved lean tissue to fat ratios. Animal growth may comprise growth overall during the course of the animal's life or in a pen prior to slaughter. Animal growth in the context of the present invention is primarily measured in terms of weight gain, although other measures are not excluded.

In the experiments carried out to date, and detailed below, the applicants have also surprisingly found that selected antistress agents discussed above, or combinations thereof, when administered to an animal can promote production gain in an animal beyond what might be anticipated from reduction in stress alone.

Accordingly, in a further aspect the invention provides a method of promoting production gain in an animal, the method comprising administering to said animal at least one antistress agent. The present invention also provides the use of antistress agents as discussed above as production gain promoters. The use may be in the preparation of a composition for use as a production gain promoter in animals. The compositions may range from feedstuffs to any of the therapeutic compositions discussed above. The antistress agents to be administered comprise any of those agents or compositions referenced above. Administration dosage levels and protocols are similarly discussed above.

Conveniently, the antistress agents may be used in animal feedstuffs to achieve the growth promotion benefits. Examples of suitable feedstuffs include hay, silage, haylage, grain, cereals and chicory or any other animal feedstuff produced naturally or artificially manufactured.

One of the production gains identified above is the protection against or recovery from trauma.

The use of antistress agents as protective or recovery aiding agents before, during or after periods of physiological or physical stress as discussed above is specifically contemplated. The use of antistress agents in conjunction with surgery, injury or trauma may be desirable. Examples of trauma include myocardial infarction and cerebrovascular accidents (strokes and brain haemorrhage) but are not limited thereto. That is, the antistress agent may have protective function, especially an organ protective function in the case of physical or psychological stress. Recovery may be conveniently measured through liveweight loss or gain subsequent to injury, surgery or trauma. Animals treated with antistress agents before surgery generally demonstrated no loss in weight, or positive gains compared with weight losses in animals not so treated.

Methods of treating an animal to prevent or aid recovery from stress, particularly surgery or trauma, comprising administering one or more antistress agents alone, or with one or more other therapeutic agents or compositions is therefore contemplated.

The present invention also extends to the use of antistress agents as adjuvants for therapeutic agents. The use may comprise the concurrent or sequential administration of one or more antistress agents with the therapeutic agent(s). Suitable agents and administration protocols are as discussed above.

The use of the antistress agents may also be in the preparation of a composition for use in animal treatment. Examples of such compositions include drenches, vaccines, anthelmintics and the like as discussed above.

In a still further aspect, the invention provides a method of treating an animal, the method comprising administering a therapeutic composition of the invention to said animal. In a preferred method of treatment, the animal is an animal infected with helminths and the therapeutic composition is an anthelmintic composition. Again, any of the compositions and administration regimes referenced above may be employed in this method of the invention.

The applicant has also discovered that the effectiveness of therapeutic agents, especially anthelmintics can be enhanced through the use of substances which increase nitric oxide levels. The applicants hypothesised that the effectiveness of the antistress agents was in allowing natural (endogenous) nitric oxide to facilitate anthelmintic treatment.

Results from the studies conducted suggest that nitric oxide can reduce gut parasite numbers. It seems very likely that this effect occurs via an inflammatory process briefly making the gut wall inhospitable to infestation. Cortisol, the stress hormone, counteracts the effects of nitric oxide and other inflammatory mechanisms. A second route for the generation of immune response to parasites may involve the liberation of certain long chain amino acids from muscle tissue. This amino acid liberation is a known trigger for immune response, and humans with muscular atrophy or high levels of stress are poor at such mobilisation. Acute or chronic stress in animals may thus suppress both this muscle origin and nitric oxide generated immune response and in doing so reduce their synergistic efficiency in decreasing parasite numbers.

The applicants, while not bound by this hypothesis, have shown that exogenously applied substances that promote nitric oxide levels can on their own facilitate anthelmintic treatment.

Accordingly, in a further aspect the invention provides a second therapeutic composition comprising a therapeutic agent and a nitric oxide promoter.

The therapeutic agents include any of the agents discussed above. The nitric oxide promoter may be selected from groups known in the art including L-arginine, diethylamine nitric oxide complex, sodium nitroprusside and S-nitroso-N-acetylpenicillamine amongst others. Appropriate dosage rates range from 0.00001 g/kg livewight to 0.01 g/kg. A preferred range is from 0.0005 to 0.0005 g/kg, preferably 0.0001 g/kg. The compositions may be formulated and administered as discussed above for the first therapeutic composition.

A method of treating an animal using this second therapeutic composition by administering same also forms part of the invention.

Utility

It will be appreciated from the foregoing discussion that antistress compounds with their potential to promote a broad range of production gains have clear utility in farming, pet care, zoos and animal based industries generally. Major economic and welfare implications are also apparent.

Reduction in animal stress will allow animals to better cope with their environment. This may increase life expectancy, weight and reproductive ability to name a few factors.

Where growth rates can be increased, the time taken for animals to attain required slaughter weight can be reduced, as can feed costs, the two major overheads in the system. For example, in intensive production systems, the most important economic factor is the efficiency of feed conversion or the feed conversion ratio (FCR). Between 60% and 70% of total overheads in the two systems are feed costs, so any procedure or treatment that would increase the efficiency of feed conversion, and thus increase growth rate, would have a major economic impact.

The results obtained also suggest that animals kept at sub-optimal temperatures and given antistress compounds approach and even surpass the FCR and weight gains observed in control animals. There is potential use in reducing heating costs especially in the poultry industry.

Additionally, the use of antistress compounds with performance enhancers, vitamin C and amino acids or combinations thereof can improve production gains and therefore economic returns to farmers.

Other production gains of importance include the ability to generate more lean and less fatty meat. This meets with consumer demand for more healthful meat products. It also has implications for humans wishing to achieve fat loss and lean tissue gain.

The invention will now be described with reference to the following non-limiting examples.

Sheep Trials

In a first series of experiments, sheep were divided into pairs from initial twins. All the animals were grazed together, on the same paddocks, from pairing through to the end of the trial. They were thus exposed to the same potential parasite load and the same access to feed and water. The animals were also genetically similar (i.e at least one shared parent). Experiments were begun when the animal was 3 months of age.

Animals had ad libitum access to grazing, water and supplementary feed such that intake was never limited.

EXPERIMENT 1

One half of the pairings were rounded up once a week and run through a race (control group). Any normal farm maintenance that was needed was done at this time, so that the time that animals may have been held was variable from week to week but consistent across the entire group and with the experimental group (see below). Faecal samples were also collected and both total egg and nematode egg counts calculated, and visual inspection for ectoparasites made.

The other half of the pairings (chronic stress group) were exposed to the same handling three times a week (consistent with the single weekly procedure above) and in addition to this were run around a paddock by either a human or dog (alternating) for 10 minutes. In this manner a mild, chronic, handling stress was imposed on these animals. Races and handling facilities were cleaned between animal movements to avoid any risk of parasitic contamination.

Animals were subject to the same anthelmintic treatments consisting of three pour-on (Ivomec pour on, MSD 1 ml per 50 kg), three oral (Endex, Novartis—1 ml per 5 kg) and three injectable treatments (levamisole. 7.5 mg/kg) per year (every four months).

As can be seen from FIG. 1 parasitic load during the course of the year was far greater in the stressed group, and growth rate was less than the control group, and the duration of knockdown of parasitic numbers for the set anthelmintic dosage less.

EXPERIMENT 2

In a similar parallel experiment the control group was identical and the paired group to this control (acute stress) received identical treatment to the control group and in addition an acute stress one day prior to anthelmintic treatment. This consisted of chasing the group three times during the day with a dog for 15 min duration each time. The faecal egg count and ectoparasite assessment was the same in both groups at time of the first experimental anthelmintic treatment. Anthelmintic treatment was administered at the same dosage as one of the four monthly treatments above and then faecal eggs counts followed for up to 6 months, with no further treatment. At average nematode counts of 600–700 treatment is recommended. It can be seen from FIG. 2 that the knock down time (time following the treatment in which egg counts were maintained below this acceptable number) was less in the acute stressed group. Again growth rate was less in the stressed group.

For both experiment 1 and 2 each group of animals were then crossed-over in experimental treatments (i.e. each group received the treatment of its counterpart). A similar treatment dependent effect on anthelmintic efficacy emerged.

EXPERIMENT 3

In a similar set of experiments to experiment 1, the animals in the chronic stress group also all received a chemical substance metyrapone (in an oral form at 5 mg/kg live weight) at the time of anthelmintic treatment. This substance is known to suppresses some of the physiological stress responsiveness, including elevation of levels of the glucocorticoid hormone cortisol.

Figure 3:
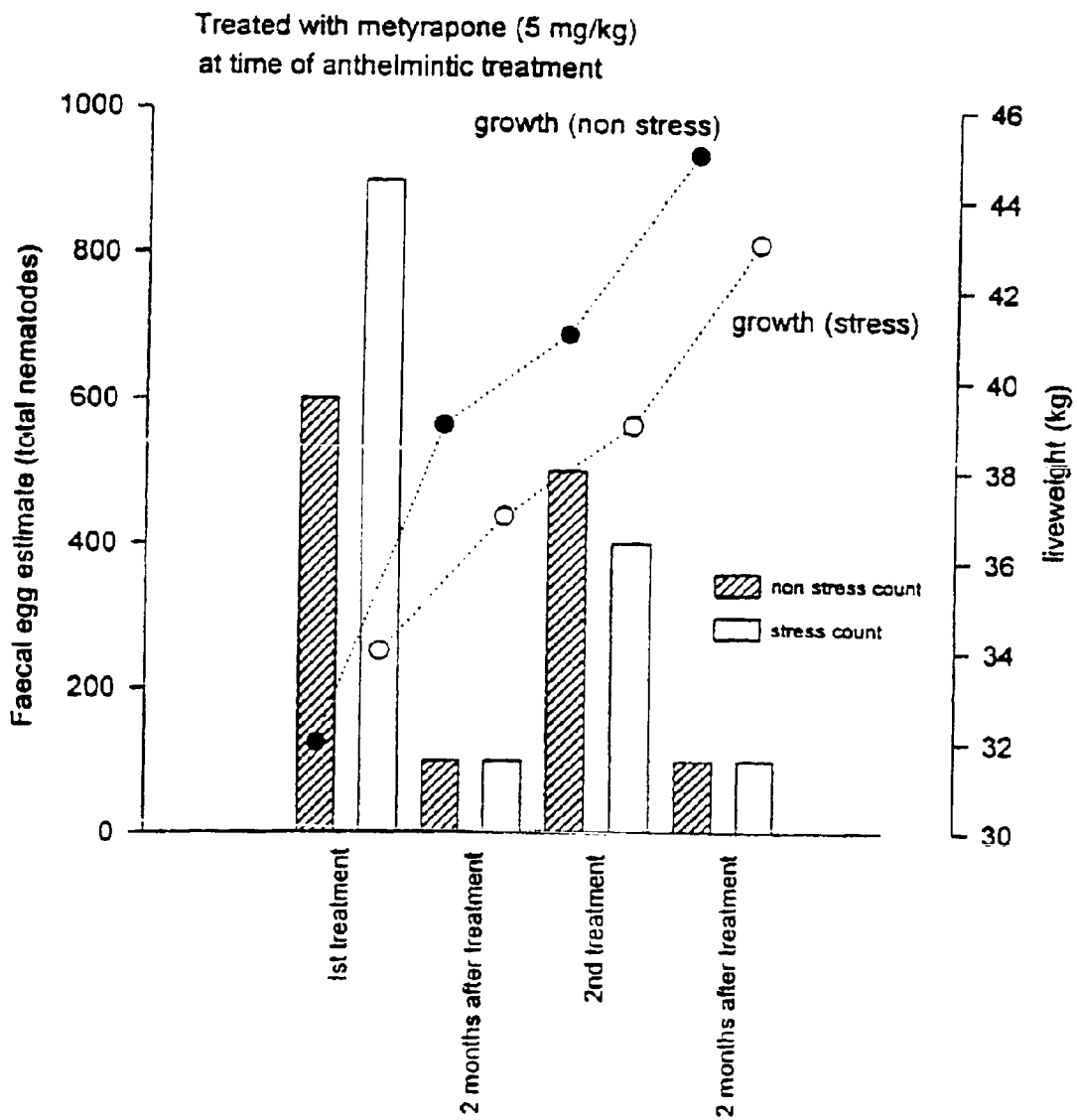
FIG. 3 is a bar graph with a superimposed line graph depicting the level of faecal egg estimates on the bar graph and animal growth on the line graph for chronically stressed animals treated with metyrapone.
Figure 6A:
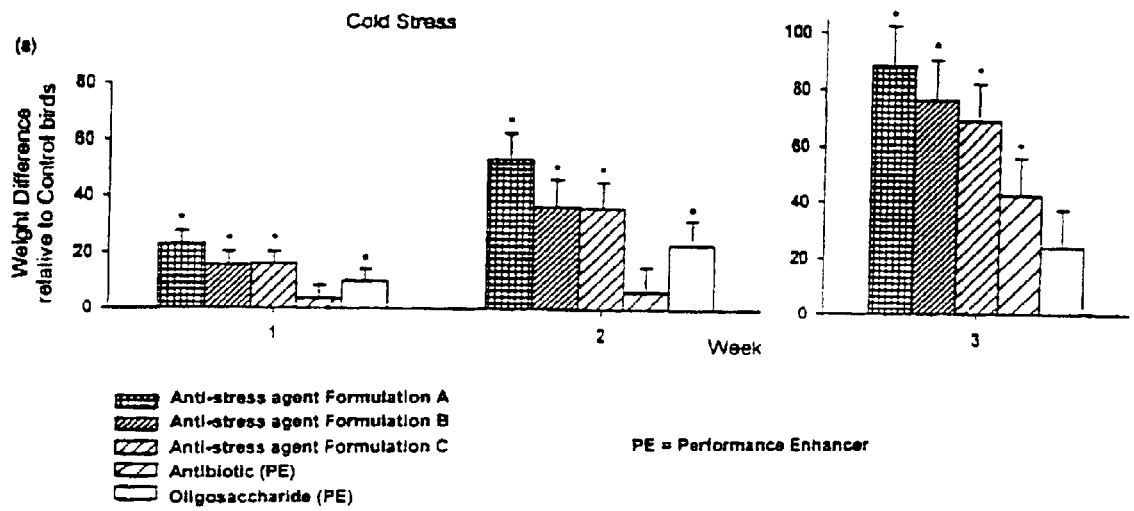
FIG. 6(a) is a bar graph which shows the differences in average weight of broiler chickens (+/−SED) relative to control birds in treatment groups exposed to cold stress (28° C. temperature during weeks 1 and 2). All groups were removed to 21° C. after 2 weeks. Symbols above columns represent significant differences in weight (*$P<0.05$; +$P<0.01$; *$P0.001$) from control birds.
Figure 6B:
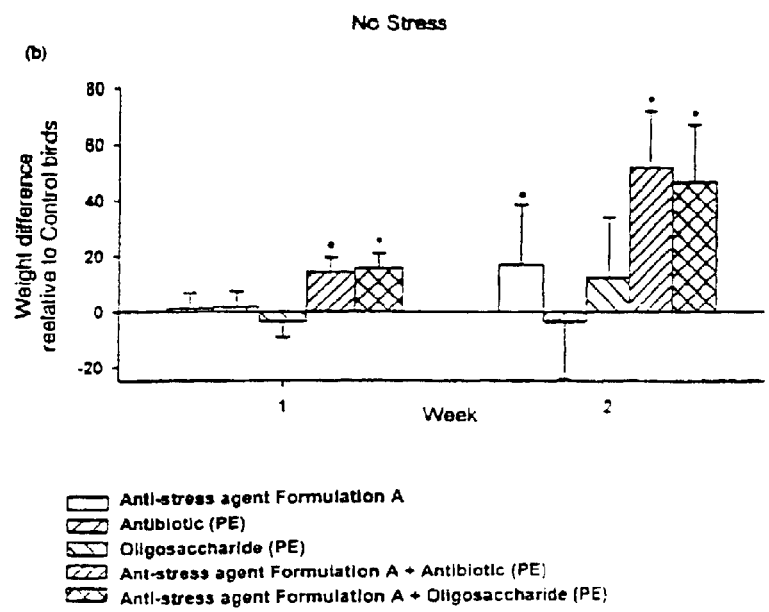
FIG. 6(b) is a bar graph which shows the differences in average weight of broiler thickens (+/−SED) relative to control birds in treatment groups maintained at optimum temperature (32° C.) for weeks 1 and 2. All groups were removed to 21° C. after 2 weeks. Symbols above columns represent significant differences in weight (*$P<0.05$; +$P<0.01$; *$P0.001$) from control birds.
Figure 7:
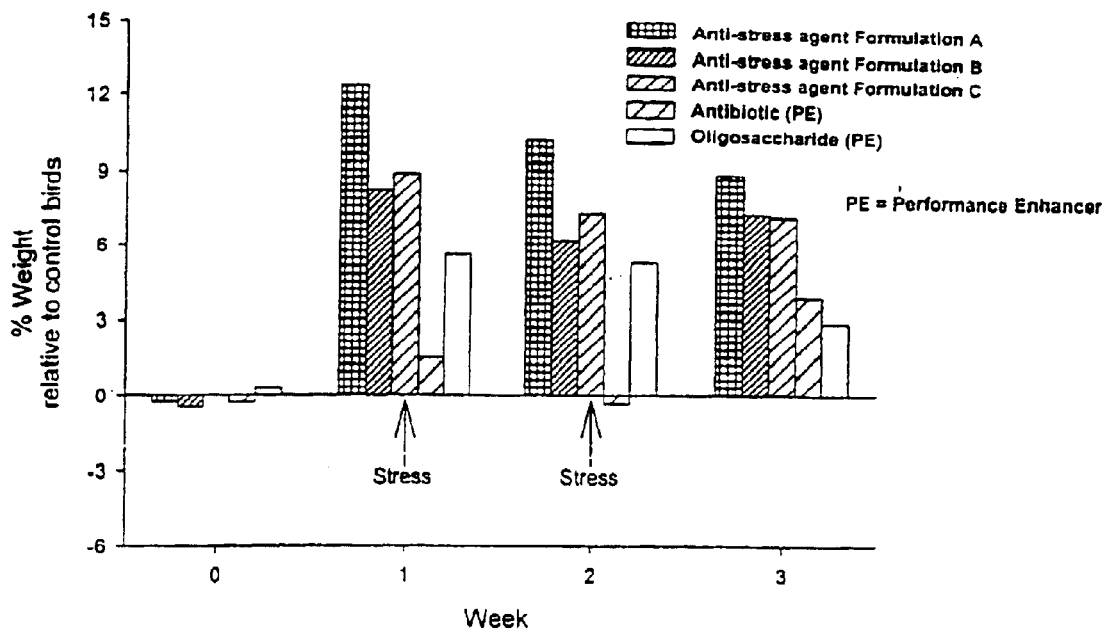
FIG. 7 is a bar graph which shows percentage differences in average weight of broiler chickens relative to control birds in treatment groups exposed to cold stress (28° C.) during weeks 1 and 2.
Figure 8:
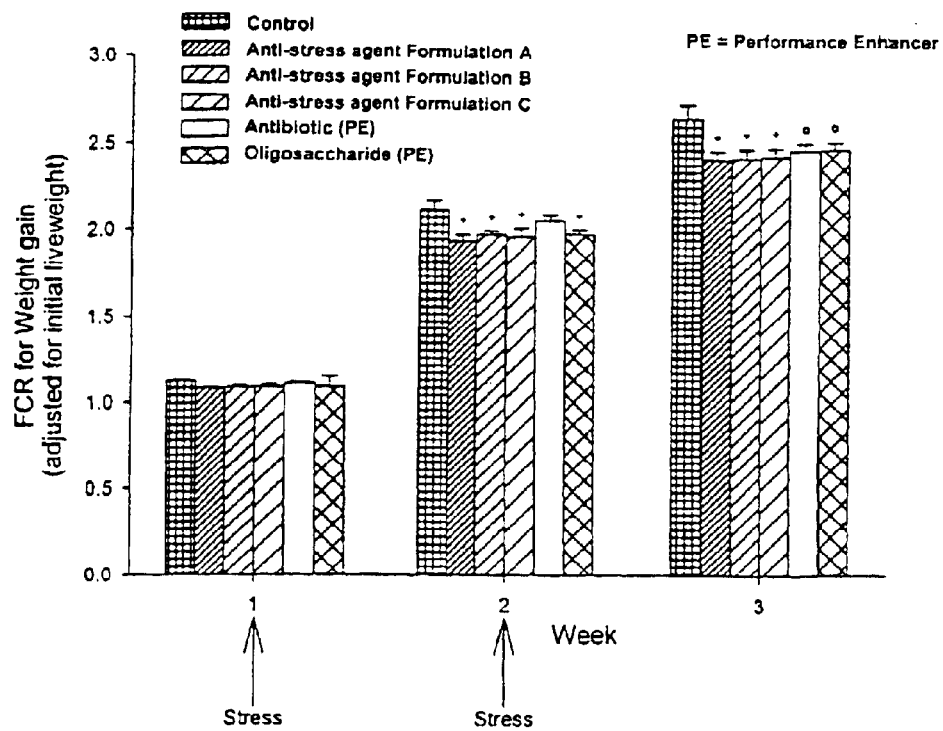
FIG. 8 is a bar graph which shows average Feed Conversion Ratio (FCR) of broiler chickens from treatment groups exposed to cold stress (28° C.) during weeks 1 and 2. Symbols above columns represent significant differences in weight (*$P<0.05$; +$P<0.01$) from control birds.
Figure 9:
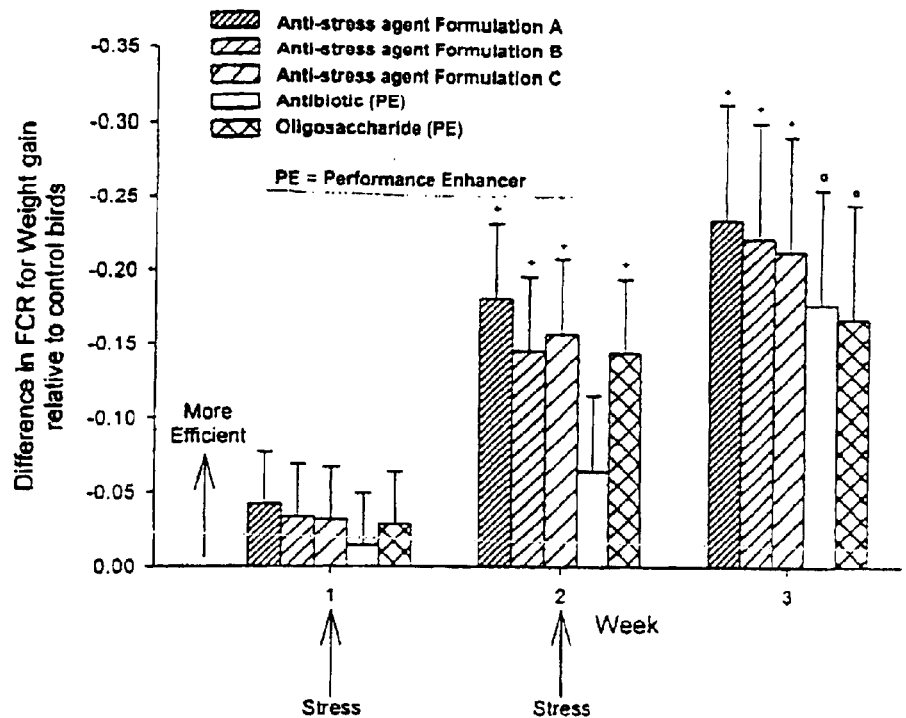
FIG. 9 is a bar graph which shows the differences in average Feed Conversion Ratio (FCR) of broiler chickens (+/−SED) relative to control birds in treatment groups exposed to cold stress (28° C.) during weeks 1 and 2. Symbols above columns represent significant differences in weight (*$P<0.05$; +$P<0.01$) from control birds.

Animals that received this treatment showed the same efficacy of anthelmintics as the non-stressed groups and similar growth rates. FIG. 3 illustrates this data.

EXPERIMENT 4

The acute versus control groups of experiment 2 were also repeated with the acute group receiving metyrapone as above. Again no differences were seen between the acute and control groups when metyrapone was administered.

EXPERIMENT 5

This was again a repeat of experiment 2 but also included the chronic stress group. One treatment was given including metyrapone to stressed (acute and chronic) animals and the time until nematode counts exceeded recommended number for dosing followed. With meryrapone treatments both chronic and acute stressed animals showed no differences to the control group (FIG. 4).

EXPERIMENT 6

In this experiment two groups were set up as per the original control groups in experiment 1 (i.e. no additional stresses) and were treated as per anthelmintics in this experiment (i.e. 4 treatments per year). In addition one of these control groups received metyrapone (5 mg/kg) at the time of anthelmintic treatment.

Growth rate over the year was compared. The control group that received no metyrapone showed a net gain of mean 12 kg and standard deviation 3 kg. The metyrapone treated group showed 18 kg mean and standard deviation of 2 kg. The results are shown in FIG. 5.

EXPERIMENT 7

Poultry Methodology

Objective

This work aimed to investigate the effectiveness of an antistress containing composition or a stress alleviating composition (conveniently referred to as "SAC"), (7-methyl-1,2-di-3-pyridyl-1-propanone, vitamin C and long chain amino acid mix) versus a calorie adjusted control, in lowering the physiological responses to stress and promoting growth in an intensive production systems (broiler chickens). In addition, the effect of the SAC agent in combination with existing industry feed additives (Performance enhancers: antibiotics and indigestible carbohydrates (oligosaccharides) was investigated in broiler chickens.

432 day-old male broiler chicks were used in the experiment carried out over six weeks in a poultry research unit. Chicks were assigned at random to one of 12 groups:

Group 1—Control 32° C. (n=36)
Group 2—Control 28° C. (n=36)
Group 3—Experimental Formulation A 32° C. (n=36)
Group 4—Experimental Formulation A 28° C. (n=36)
Group 5—Experimental Formulation B 28° C. (n=36)
Group 6—Experimental Formulation C 28° C. (n=36)
Group 7—Performance Enhancer 32° C. (n=36)
Group 8—Performance Enhancer 28° C. (n=36)
Group 9—Oligosaccharide 32° C. (n=36)
Group 10—Oligosaccharide 28° C. (n=36)
Group 11—Experimental Formulation A+Performance Enhancer 32° C. (n=36)
Group 12—Experimental Formulation A+Oligosaccharide 32C (n=36)

Once selected, groups of 6 birds were housed per cage in heated brooders (i.e. One treatment group (36 birds) per 6 cages). Each group had access to pelleted feed (NRM New Zealand) in excess of requirements during the trial conforming to standard poultry use Ross broiler specification), and water was freely available. During the manufacturing of the feed the following treatments were included.

SAC Agent (2-methyl-1,2-di-3-pyridyl-1-propanone, vitamin C, valine, isoleucine and leucine mixture), mixed with a glucose-based polymer carrier (0.01 g drug to 1 g of carrier) before addition to the feed in the following doses.

Formulation A (per kg feed):
0.01 g 2-methyl-1,2-di-3-pyridyl-1-propanone
0.1 g Vitamin C
5 mg Valine, isoleucine and leucine Formulation B (per kg feed):
0.005 g 2-methyl-1,2-di-3-pyridyl-1-propanone
0.05 g Vitamin C
0.5 mg Valine, isoleucine and leucine Formulation C (per kg feed):
0.001 g 2-methyl-1,2-di-3-pyridyl-1-propanone
0.01 g Vitamin C
0.1 mg Valine, isolcucine and leucine Performance Enhancers:
(Avilamycin (Surmax): Elanco Animal Health, Indianapolis, USA)
Dose: <0.2 g/kg (antibiotic concentration of 0.1 (g/ml).
Mannan oligosaccharide—indigestible carbohydrate (Bio-Mos: Alltech, Inc.USA)
Dose: 1 g/kg Daily feed intake was recorded for each group of birds, and all birds were weighed weekly.

Birds were either kept at optimum temperature levels (32° C.) or exposed to cold stress (28° C.) from day 1 until day 14 of the trial. After 14 days they were removed to larger raised horizontal cages where all groups were maintained at 21° C. The birds remained in these cages for the remainder of the trial after which time they were slaughtered. After slaughter, meat from 6 birds per group was analysed for fat composition.

Results

The SAC increased growth rates in broiler chickens exposed to cold stress.

Significantly (P<0.001) heavier birds were recorded in the groups receiving SACs. The effect was apparent after only one week of cold stress, and SAC treatment, and was maintained for a week following stress removal.

Three formulations of the SAC were used in the trial and the patterns of their effect, relative to control birds, were slightly different.

Birds receiving Formulation A were 22.9 g (12.9%) heavier than control birds after 1 week of cold stress (P<0.01), 53.7 g (11.2%) heavier at the end of the cold stress period (week 2; P<0.001), and 89.3 g (9.5%) heavier after 3 weeks of the trial (P<0.001).

Birds receiving Formulation C showed a similar, but less dramatic, pattern of growth both during the period of cold stress—week 1: 16.1 g (9%: P<0.01); week 2: 36.5 g (7.6%: P<0.001), and after the stressor was removed (week 3: 68.7 g (7.3%: P<0.001); week 4: 58.5 g (3.6%: P>0.05).

Birds receiving Formulation B responded with significantly increased weight gain relative to controls for the first 4 weeks of the trial (week 1: 15.8 g (8.9%: P<0.01); week 2: 36.9 g (7.7%: P<0.001); week 3: 77.0 g (8.2%: P<0.001); week 4: 101.7 g (6.3%: P<0.05).

In comparison to birds given the SAC, birds receiving performance enhancer antiobiotic or oligosaccharide and exposed to cold stress had a lower rate of growth. This was obvious both during the period of cold stress, and afterwards when the birds were transferred to optimum conditions.

However, birds given oligosaccharide performance enhancer were significantly (P<0.05) heavier than control birds during the period of cold stress (week 1: 9.6 g (5.3%): week 2: 23.2 g (4.8%)). This effect declined rapidly when the stressor was removed, and by the end of the trial birds receiving the oligosaccharide were lighter on average than birds in the control group (2223 g vs. 2254 g).

The weights of birds receiving the antibiotic performance enhancer were not significantly different (P>0.05) to control birds during the period of cold stress (week 1: 3.5 g (2.0%): week 2: 6.3 g (1.3%)). However, when the stressor was removed, the birds showed a significant (P<0.01) increase in weight relative to control birds (week 3: 42.6 g (4.5%)), although the effect was not maintained during the remainder of the trial (week 4: 35.2 g (2.2%).

The increased growth rate due to SACs was not associated with a corresponding increase in feed intake.

Treatment with a combination of Formulation A of the SAC and performance enhancer or oligosaccharide increased the efficiency with which the feed was utilised for weight gain Feed Conversation Ratio (FCR).

Birds that received a combination of Formulation A of the SAC and antibiotic or oligosaccharide performance enhancer consistently showed more efficiency at feed conversion throughout the trial.

Birds given the SAC in combination with the antibiotic performance enhancer were 0.030 (2.8%) more efficient at feed conversion than control birds after 1 week of the trial and 0.179 (8.6%: P<0.05) more efficient after 2 weeks.

Similarly, birds given the SAC in combination with the oligosaccharide performance enhancer were 0.022 (2.1%: P<0.01) more efficient than control birds after 1 week of the trial and 0.190 (9.2%: P<0.05) more efficient after 2 weeks.

FIGS. 5 to 8 summarises some of this data.

Conclusions

The trial established that the SAC could increase growth rates in chickens.

This increase in growth rate appeared to be achieved entirely by a reduction in the physiological stress response, or stimulation of another growth pathway. The intensive production system for chickens utilises raised platforms or cages to raise the animals, minimising the potential for parasitic infection. The most significant difference to control was seen in stressed animals suggesting that at least part of the effect was due to modification (reduction) of stress effects on growth.

The SAC appeared to work by increasing the efficiency by which feed was converted into body weight.

Fat analysis of broiler chicken carcasses indicated that the SAC reduced the amount of fat deposited in response to the cold stress.

The data also suggests that broiler chickens kept at sub-optimal temperatures (cold stressed) and given the SAC approach, and even surpass, the efficiency of feed conversion to weight gain observed in control birds at optimum temperatures (1.078 vs 1.068 after 1 week of cold stress: 1.930 vs 2.071 week 2).

EXPERIMENT 8

This experiment was carried out at a pig research until over 8 weeks. 54 one month-old pigs (27 entire males and 27 females) were assigned at random to one of 6 sex-balanced treatment groups (either 5M:4F or 4M:5F):

Treatment 1—Control: low stress (n=9)
Treatment 2—Control: high stress (n=9)
Treatment 3—Experimental Formulation A: low stress (n=9)
Treatment 4—Experimental Formulation A: high stress (n=9)
Treatment 6—Experimental Formulation B: high stress (n=9)
Treatment 6—Experimental Formulation C: high stress (n9)

Groups of 3 animals were housed per pen on weaner flat decks maintained at 28–30° C. Each group had access to a commercial-type grower meal and mineral/vitamin supplement (Tasmix pig grower vitamin/mineral premix: Tasmax Vaccines Ltd, Auckland, New Zealand), in excess of daily requirements from a hopper placed in each pen. Daily feed intakes were recorded for each group of animals and water was freely available.

Two levels of stress were imposed on the animals.

Groups 1 and 3: Low level stress associated with normal daily cleaning and feeding and weekly weighing.

Groups 2, 4, 5, and 6: Additional stress imposed on the animals by mixing each group twice weekly. One animal from each of the three groups comprising each treatment was interchanged immediately after weighing.

All animals were weighed twice weekly, before being orally dosed with either formulations of the anti-stress agent (Groups 3–6) or calorie adjusted vehicle (Groups 1 and 2). The pigs remained in pens on the weaner decks for 8 weeks before being slaughtered.

The SAC (2-methyl-1,2-di-3-pyridyl-1-propanone, vitamin C, valine, isoleucine and leucine mixture) was mixed with a glucose-based polymer carrier (0.01 g drug to 1 g of carrier), before being dissolved to give the following doses.

Formulation A (per kg bodyweight):
0.5 mg 2-methyl-1,2-di-3-pyridyl-1-propanone
5 mg Vitamin C
5 mg Valine, isoleucine and leucine
Formulation B (per kg bodyweight):
0.1 mg 2-methyl-1,2-di-3-pyridyl-1-propanone
1 mg Vitamin C
1 mg Valine, isoleucine and leucine
Formulation C (per kg bodyweight):
0.05 mg 2-methyl-1,2-di-3-pyridyl-1-propanone
0.5 mg Vitamin C
0.5 mg Valine, isoleucine and leucine Faecal samples were collected after weeks 1 and 5 and the gastro-intestinal tract of each animal was retained after slaughter to assess the parasite loads of each animal throughout the trial.

Results

During the initial weaning period, a major stress for pigs, control pigs all exhibited significant weight loss. In contrast pigs on formulations A and C gained weight, while pigs on formulation B did not. This suggests that the right doses of the compounds may prevent stress related to weaning loss of growth in piglets.

Piglets treated with Formulations A and C continued to show increased weight gains and reached goal weights faster compared to control and animals treated with dose B during the course of the mild stress experiment.

Figure 10:
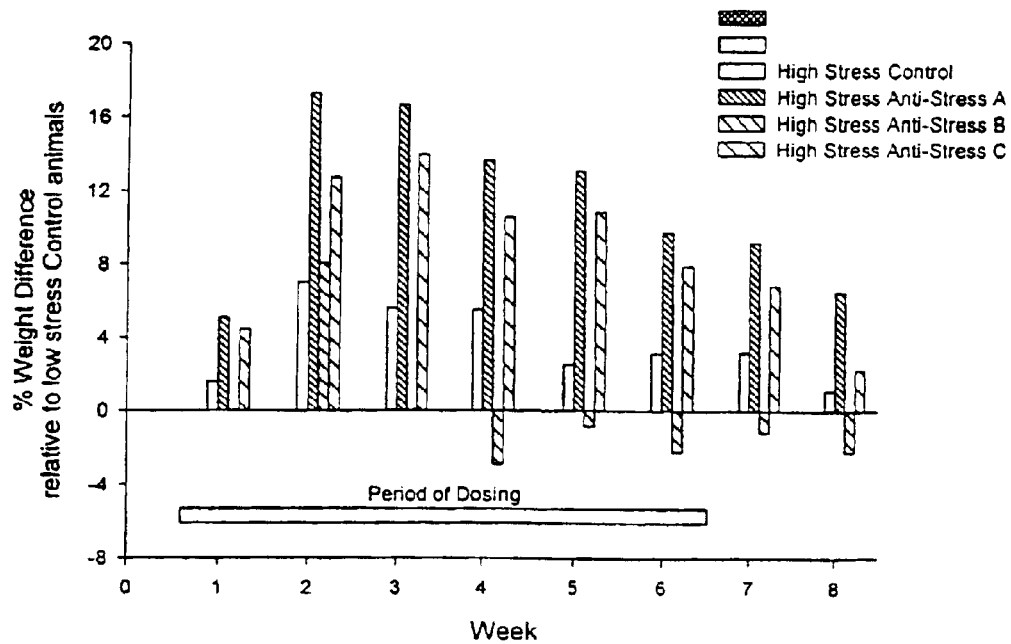
FIG. 10 is a bar graph which shows percentage differences in average weight of pigs relative to low stress control animals and adjusted for initial liveweight, breed and sex, maintained under high and low stress conditions and orally dosed with either three concentrations of anti-stress compound or sugar carrier alone. Bar represents 6 week period when animals were dosed.
Figure 11:
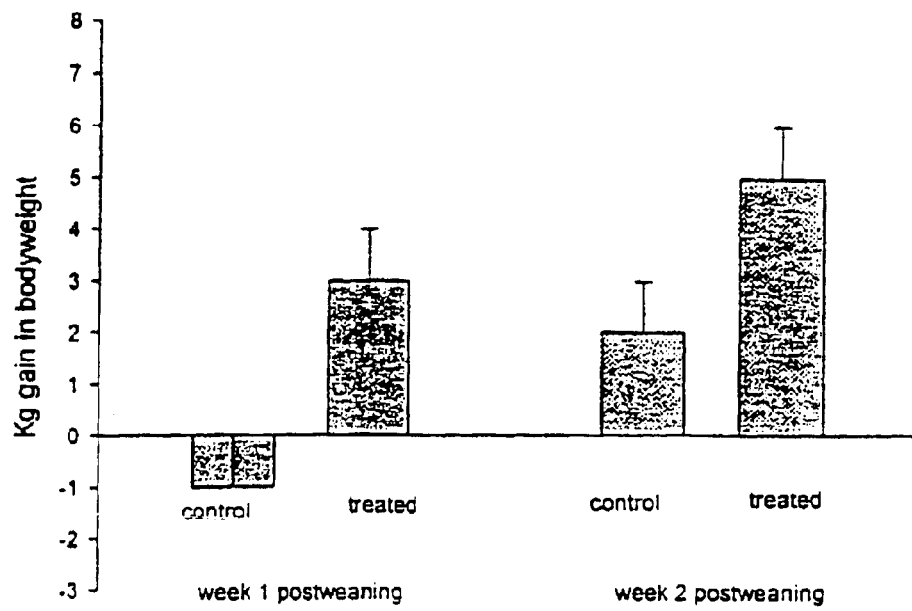
FIG. 11 is a bar graph which shows gain in weight for the first two weeks after weaning in control animals or animals treated with the experimental compound at the highest doses (Formulation A). Mean and standard deviation presented.

FIGS. 10 and 11 display this data.

EXPERIMENT 9

Dose Response and Dose Composition Relationships

In four different species (sheep, poultry, pigs and rats) different dosages of the compound metyrapone alone or in combination with vitamin C, isoleucine, leucine, valine were tested for growth promotant effects.

These mixtures were administered by oral routes three times over six weeks and a control group was administered a glucose mix at the same time (calorie equivalent). Animal growth in terms of liveweight gains were measured over periods of time, as was feed consumed.

This data together with that described in the examples above for sheep, pigs and poultry was used to work out a dose relationship response between metyrapone and % gain in production. This % gain includes increased growth for increased feed, metyrapone and approximate increased labour costs.

Figure 12:
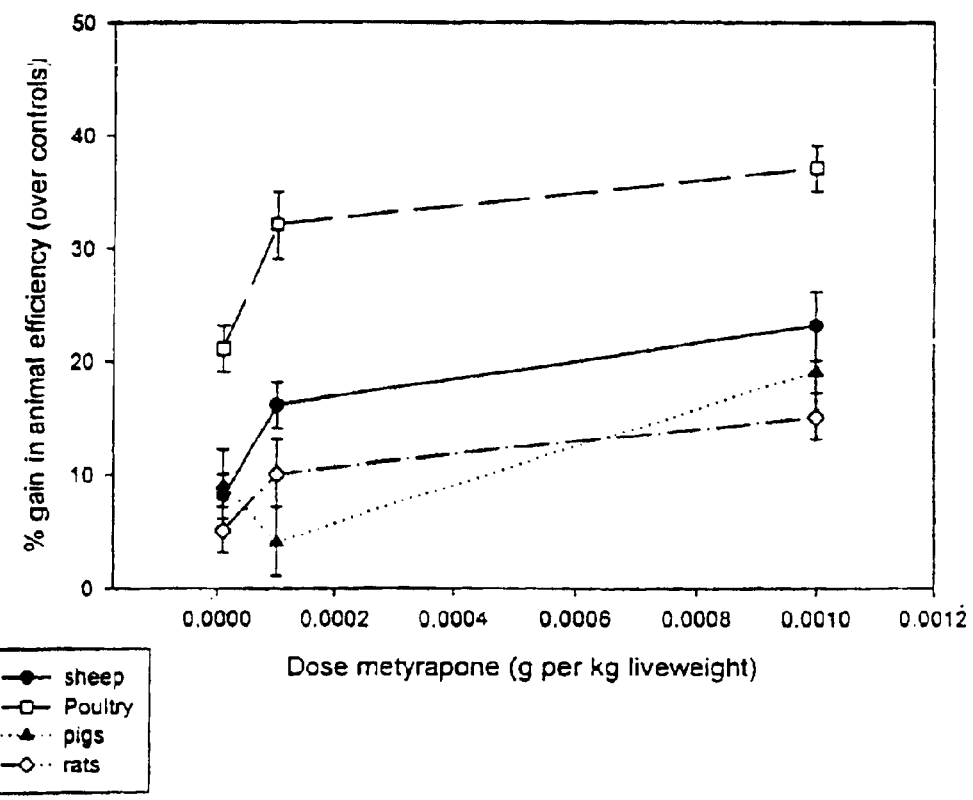
FIG. 12 is a line graph which illustrates species dose response differences to multiple dosing with metyrapone mixtures over time. Gain in efficiency calculates the gain in growth alone against increased costs due to increased feed, the metyrapone and potential increased labour costs for administration compared to non-metyrapone control counterparts. This is expressed as a % gain over these control animals. Mean and standard deviation (sd) presented.

In all species except pigs an increase in gain was seen with an increase in dose of metyrapone levelling out as expected with a positive dose response curve. In pigs a low and a high dose were effective however a mid-range dose did not produce the same gains. This data is displayed in FIG. 12.

In all species the addition of vitamin C, isoleucine, leucine and valine increased the measured growth associated with metyrapone. Metyrapone alone also increased growth, except in animals that were deprived of vitamin C and long chain branched amino acids (data not shown). Vitamin C, isoleucine, leucine and valine had a small growth promotant effect in mildly nutritional deprived animals. It is possible that a certain level of these amino acids and vitamin C are needed for metyrapone to have its maximal effect.

A synergistic growth promotant effect of a mix of vitamin C, isoleucine, leucine and valine is thus suggested. Proportional mixture of these compounds seems important, with the most successful mixture being one of approximately: 0.1 g vitamin C and 0.005 g each of valine, isoleucine and leucine to each 0.01 g of metyrapone.

Figure 13:
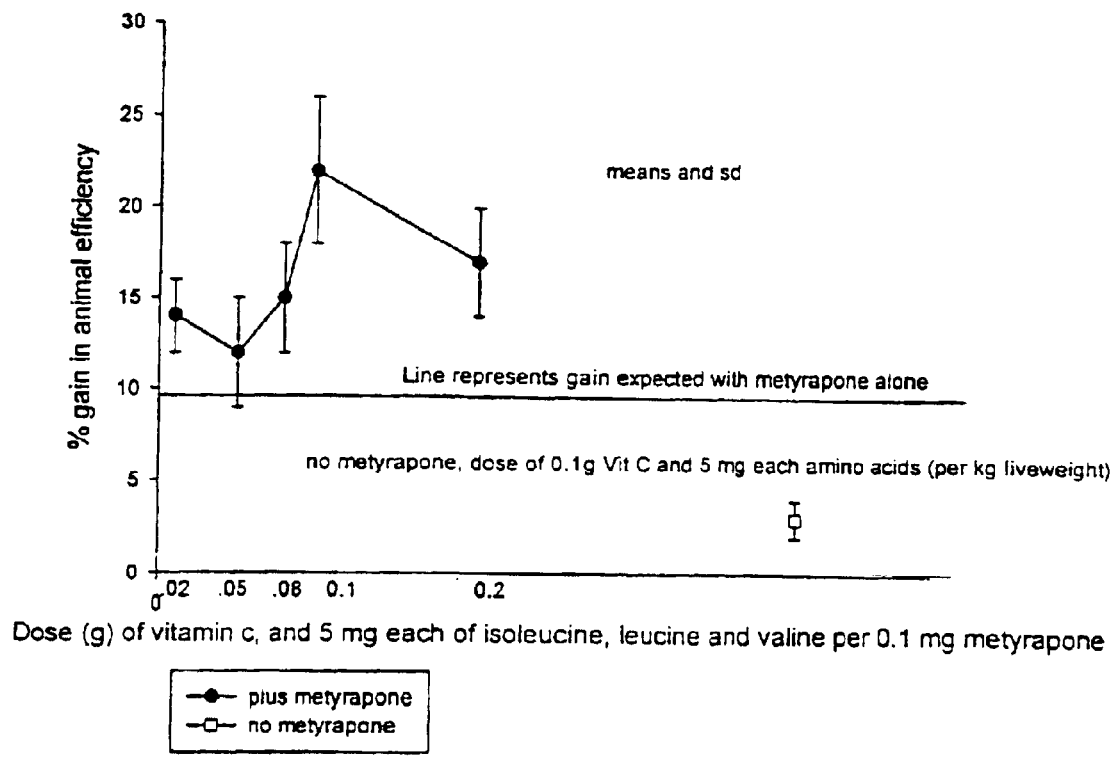
FIG. 13 is a line graph which illustrates the synergistic effect of vitamin C, isoleucine, leucine and valine on the effects of metyrapone in sheep. Also shows the slight gain from vitamin C, isoleucine, leucine and valine alone without metyrapone.

FIG. 13 demonstrates the increased gain in metyrapone effect from the addition of a range of dosages of vitamin c, isoleucine, leucine and valine. It also demonstrates a small gain from these compounds alone.

Figure 14:
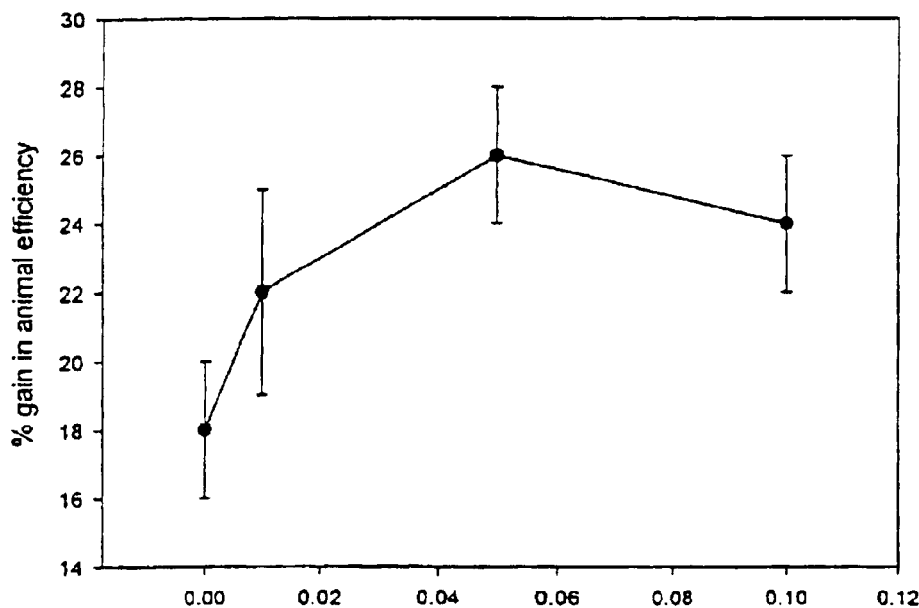
FIG. 14 is a line graph which demonstrates an increased gain by the addition of pyrollopyrimidine (mg) to 0.001 g/kg liveweight metyrapone and 0.1 g vitamin C and 0.005 g each of leucine, isoleucine and valine. Mean standard deviation displayed.

Adding a further compound, pyrrolopyrimidine to the mixture in a composition range of 0.0000001 to 10% of the metyrapone component further enhanced the effectiveness of the mixture. This is shown for sheep in FIG. 14.

Pyrollopyrimidine is known in art as a lipid transfer facilitator and it is hypothesised that addition of this compound increased the amount of effective dose of metyrapone, vitamin C, isoleucine, leucine and valine crossing cell membranes.

EXPERIMENT 10

Figure 15:
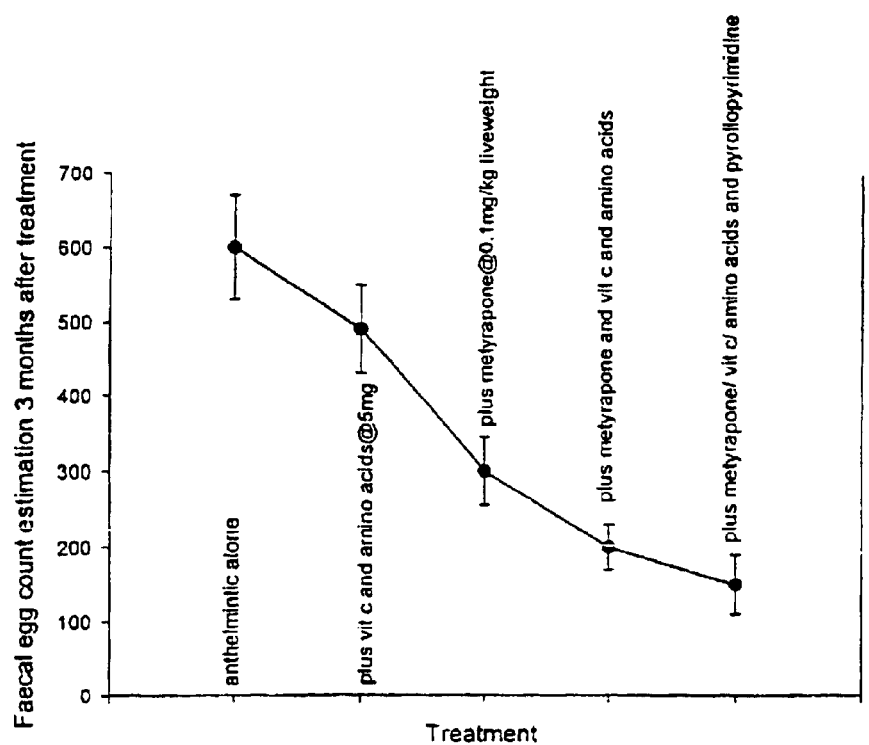
FIG. 15 is a line graph which illustrates effectiveness of metyrapone alone or in combination in increasing effectiveness of a standard anthelmintic. Mean and standard deviation displayed.

In a further experiment similar to that described in experiments 3 and 4 the increased anthelmintic effect from vitamin C, isoleucine, valine and leucine alone or in combination with metyrapone, and metyrapone and pyrrolopyrimidine was tested. Anthelmintics and these agents were given every four months and faecal count calculated each month in between treatments. FIG. 15 demonstrates the results which clearly show that treatment with an anthelmintic and metyrapone is more effective than with the anthelmintic alone. The results were further enhanced by the addition of vitamin C, and the amino acids. Further increase in anthelmintic effect was seen when pyrrolopyrimidine was added to the latter combination. By themselves, vitamin C and the amino acids had a small effect in increasing anthelmintics effectiveness.

EXPERIMENT 11

Effects of Compounds on Reproductive Success

Figure 16:
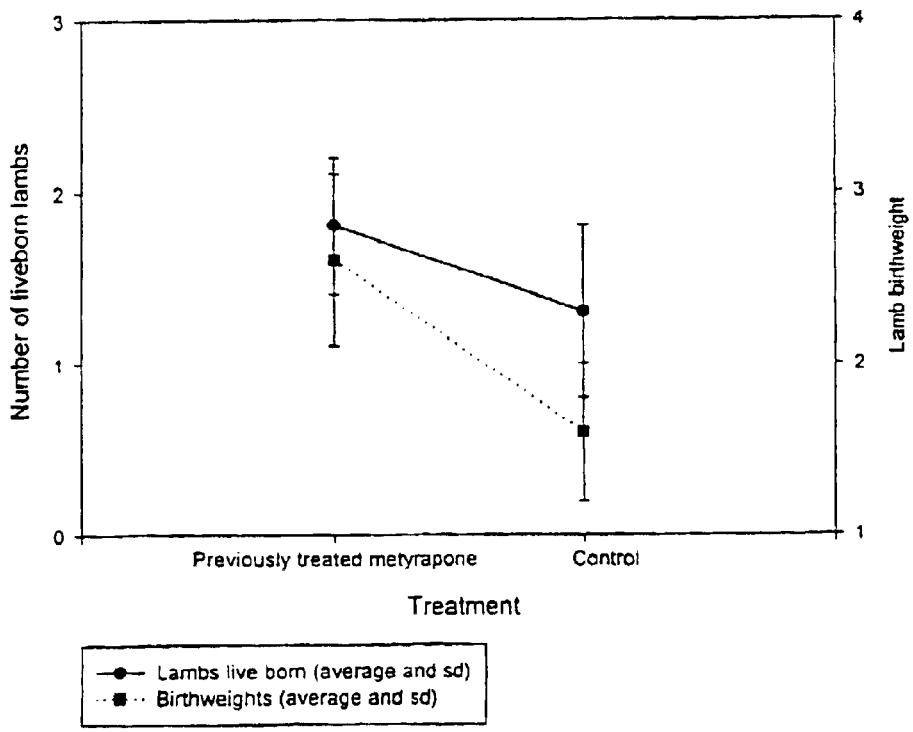
FIG. 16 is a line graph which illustrates the average number of lambs live born per ewe and average birth liveweight over 3 seasons for control ewes versus ewes previously treated with metyrapone. Mean and standard deviation presented.

Female sheep (20 ewes) chosen from original experiments in experiments 4, 5 and 6 were studied for seasonal reproductive success for up to 3 seasons following the original metyrapone treatments. These animals received no further metyrapone treatments and were kept in a flock with a similar selected group of 20 control age and weight matched counterparts that had not received metyrapone treatment. Over the 3 seasons a similar number of live born lambs were recorded for these two groups of ewes. However, the birthweight of lambs from the metyrapone treated ewes was slightly greater than seen in the control group. FIG. 16 illustrates this data.

In a separate experiment using the different sheep with no previous exposure to treatments, 20 age and bodyweight matched ewes were run as a flock. Ten of these ewes received three treatments of metyrapone and vitamin C, isoleucine, leucine and valine at a dosage of 0.001 g metyrapone/0.01 g vitamin c, 0.0005 g each of valine, isoleucine and leucine per kg liveweight in an oral form without anthelmintics. These three treatments occurred one month prior to conception, in the first and third trimester of pregnancy. The remaining ten ewes received a similar handling and control administration of a glucose-amino acid mixture.

Figure 17:
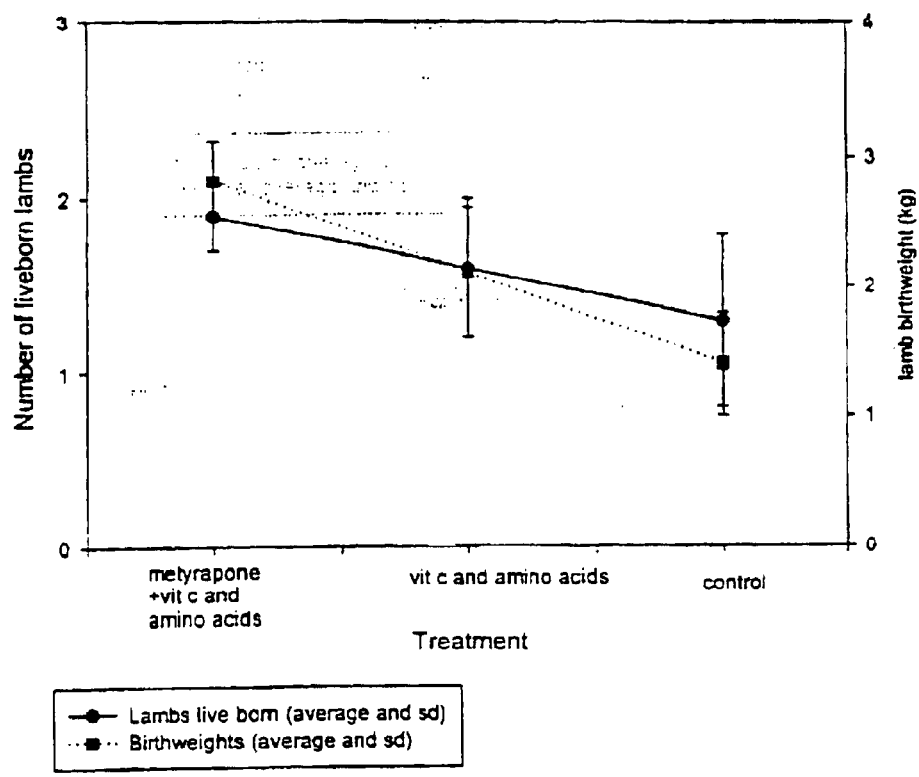
FIG. 17 is a line graph which illustrates the average number of lambs live born per ewe and average birthweight over a season with acute treatments. Mean and standard deviation.

Ewes treated with the metyrapone-vitamin C, isoleucine, leucine and valine mix recorded better reproductive success in terms of number of ewes that achieved pregnancy, number of live born lambs and birthweight of the lambs. FIG. 17 illustrates this result.

EXPERIMENTS 12

Effects of Compounds on Recovery from Surgical Stress

It has been hypothesised that stress associated with surgery may produce a slower recovery from the surgery. One potential estimate of recovery is liveweight loss or gain subsequent to surgery.

Ten ewes (liveweights 30–40 kg) and 20 rats (liveweights 300–350 g) underwent minor surgical procedures under a general anaesthesia.

Five of the ewes and 10 of the rats received a treatment of metyrapone (0.001 g per kg) combined with vitamin C (0.01 g), and valine, isoleucine, leucine each at a dose of 0.0005 g per kg. This was delivered orally 3 hours prior to surgery. The other five ewes and 10 rats received an oral glucose mixture with similar calorific properties at the same time as above prior to surgery.

Following surgery liveweights of each animal were obtained daily for 10 days.

Figure 18:
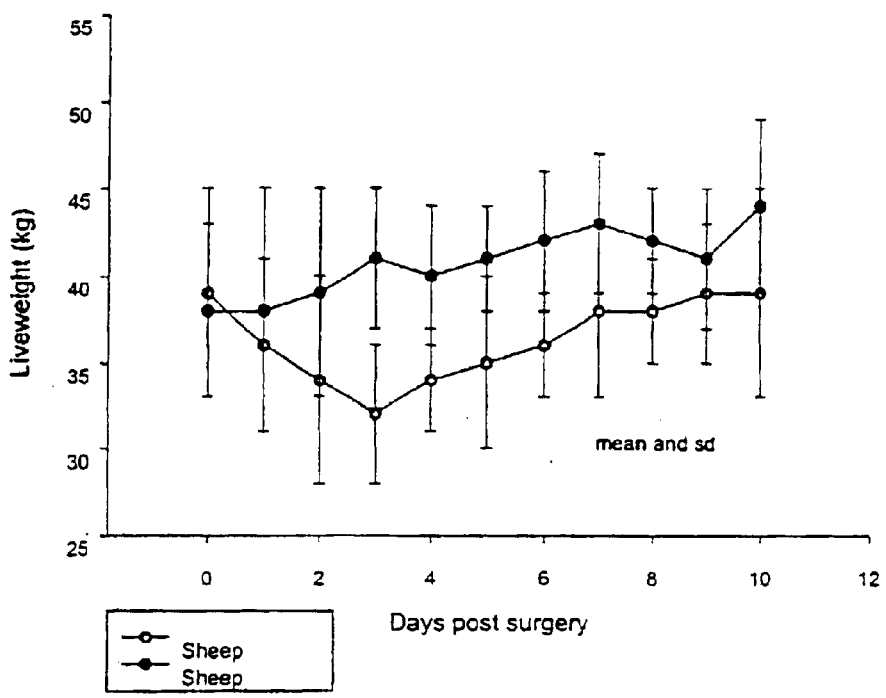
FIG. 18 is a line graph which illustrates the effects of metyrapone, vitamin C, leucine, isoleucine and valine on liveweight recovery in sheep following surgery under general anaesthesia.
Figure 19:
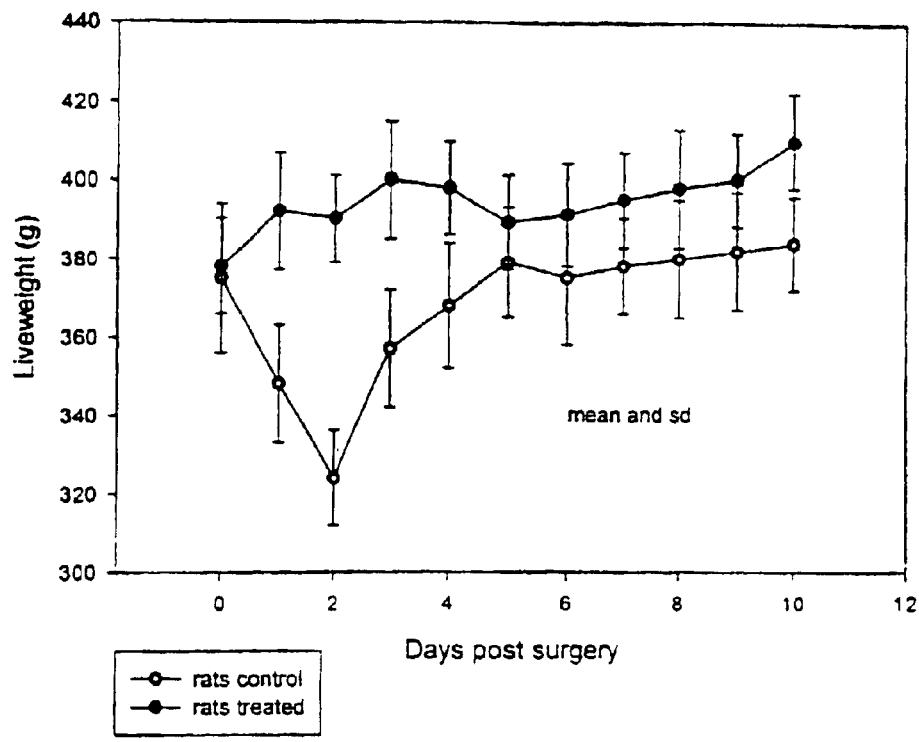
FIG. 19 is a line graph which illustrates the effects of metyrapone, vitamin C, leucine, isoleucine and valine on liveweight recovery in rats following surgery under general anaesthesia.

Control treated animals all lost liveweight for the first three to five days following surgery. None of the metyrapone, vitamin C, valine and isoleucine, leucine treated animals lost weight and many in this group gained weight over the 10 days post surgery. FIGS. 18 and 19 demonstrates this data.

EXPERIMENT 13

Effectiveness of Other Stress Relieving Compounds

In a further experiment 35 age and bodyweight matched sheep (ewes) were treated every 2 months with an anthelmintic as per experiments 3 and 4 and one of the following: mifepristone (RU 38486); proglumide; metyrapone all at 0.001 g per kg bodyweight; metyrapone at 0.0005 g combined with mifepristone (RU 38486) at 0.0005 g per kg bodyweight, metyrapone combined with mifepristone (RU 38486) each at 0.001 g per kg; and each of these plus vitamin C (0.01 g), leucine, isoleucine, valine (each at 0.0005 g), the vitamin C, isoleucine, valine and leucine mix alone or as a control calorie volume matched glucose solution. A further 7 ewes received either astressin 0.0005 g or astressin and metyrapone (astressin at 0.0005 g and metyrapone at 0.001 g) and the vitamin C and amino acid mixture as above.

Bodyweight was measured monthly and animals were treated equivalently in all other aspects.

Figure 20:
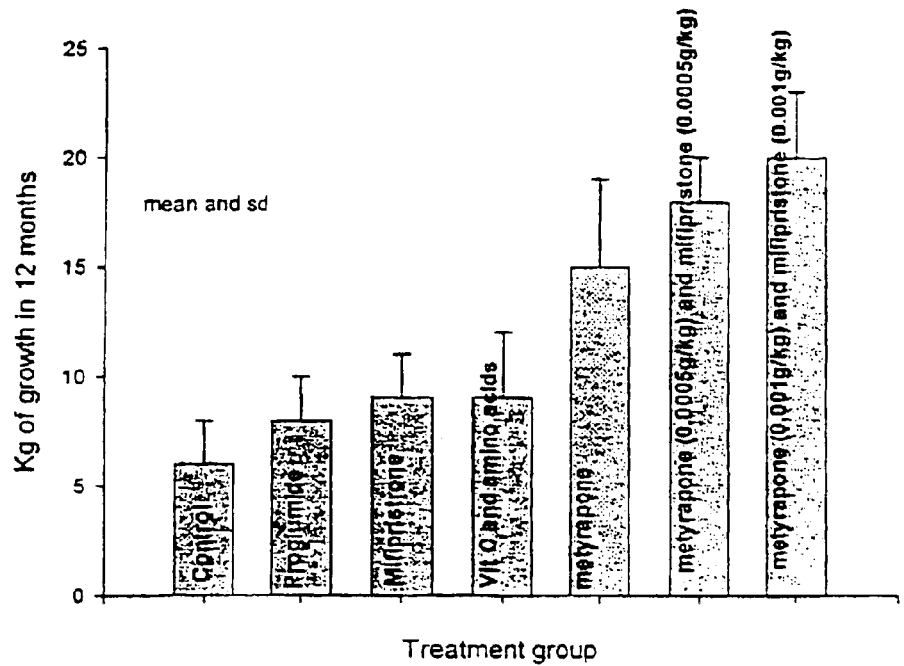
FIG. 20 is a bar graph which illustrates the different stress relieving agents administered to sheep every 2 months with anthelmintics and growth measured over a year. Mean and standard deviation is shown for each treatment group.

FIG. 20 illustrates the results obtained. Mifepristone (RU 38486), vitamin C and amino acids, and proglumide all had a small positive effect compared to control animals, metyrapone had a larger effect. Adding mifepristone (RU 38486) to metyrapone increased the positive effect slightly suggesting a synergistic and additive effect. More specifically, a 0.0001 g/kg mifepristone (RU 38486) dose alone had no effect compared to control but when added to metyrapone increased significantly the effectiveness of that dose of metyrapone, a synergistic effect. Adding control to metyrapone had no effect. At a higher dose of mifepristone (RU 38486) 0.0005 g/kg a small increase in growth over control treatments was observed. When this dose of mifepristone (RU 38486) was added to metyrapone an approximate additive effect was seen.

Astressin had similar effects but also demonstrated a large variability.

The data is usefully summarised in Table 1 below.

TABLE 1

Dose related effects of mifepristone (RU 38486) or astressin on metyrapone growth increasing properties.

| | Kg of Growth in 12 months |
|---|---|
| Control | 5 ± 3 |
| 0.0001 g/kg mifepristone | 4 ± 4 |
| 0.0005 g/kg mifepristone | 8 ± 2 |
| 0.0001 g/kg metyrapone | 13 ± 3 |
| 0.0005 g/kg astressin | 10 ± 4 |
| 0.0001 g/kg metyrapone + control | 14 ± 3 |
| 0.0001 g/kg metyrapone + 0.0001 g/kg mifepristone | 17 ± 4 |
| 0.0001 g/kg metyrapone + mifepristone | 20 ± 4 |
| 0.0001 g/kg metyrapone + 0.0005 g/kg astressin | 19 ± 5 |

EXPERIMENT 14

Effect of Compound on Lean Tissue Growth

Animals in Experiment 7 were euthanised and the lean tissue percentage of their carcasses estimated.

The method used was as follows:

SOXTEC EXTRACTION OF FAT FROM RAW MEAT (Oven dried method) was carried out according to the methods of Firth, N. L., Ross; D. A. and Thonney, M. L. (1985) Comparison of ether and chloroform for Soxtec extraction of Freeze-Dried animal tissues. Journal of the Association of Analytical Chemists 68(6): 1228–1231.

Association of Official Analytical Chemists 1995. Official Methods of Analysis 16th edition 39.1.05. (All references being incorporated herein by reference)

This method is suitable for all meat samples including those containing high levels of fat (>20%). Comparable results were obtained by the oven dried and freeze dried methods for a range of meat samples.

Principle

Samples vary greatly in fat content. Repeatedly washing the sample with petroleum ether by refluxing in a Soxtec apparatus dissolves the fat. The solubilised fat is then collected in the distillation cup and the increase in the weight of the cup represents the dissolved fat.

Sample Preparation

Approximately (3.5–4.0 g) of meat tissue is required per sub-sample. Samples were prepared in triplicate.

(1) Sample boats made by folding aluminum foil into boats approximately 10 cm×10 cm square, wipe with acetone and labelled with sample number on the outside of the foil. Disposable gloves worn when handling meat samples and boats.

(2) For frozen mincemeat—thawed in a microwave and mixed thoroughly.

For frozen whole meat—approximately 35–70 g of the frozen meat sample defrosted for 30 sec in the microwave oven. Diced into very small pieces using a knife and mixed thoroughly. Fresh samples prepared by dicing and mixed thoroughly.

(3) 3.5–4.0 g of the sample accurately weighed into the boat and the weight of the sample used recorded. (W1)

Procedure repeated for the remaining two sub-samples of the triplicate.

(NB. For high fat containing samples it is essential to fold the foil with high sides to avoid the fat leaking out).

(4) After weighing the samples were Oven Dried at 95 for 6 hours, then cooled in a dessicator.

(5) Boiling beads placed into clean labelled aluminum extraction cups and dried in a 105° C. oven for 2 hrs. After drying, the cups were cooled in a dessicator and weighed. Weight of cups recorded. (W2)

Data Handling

% Fat=(Cup wt. after extraction)−(Cup wt. before extraction)×100 Sample wt.

$$\% \text{ Fat} = \frac{W3 - W2 \times 100}{W1}$$

$$\text{Convert to Dry Matter} = \frac{\% \text{ Fat} \times 100}{\% \text{ DM}}$$

Figure 21:
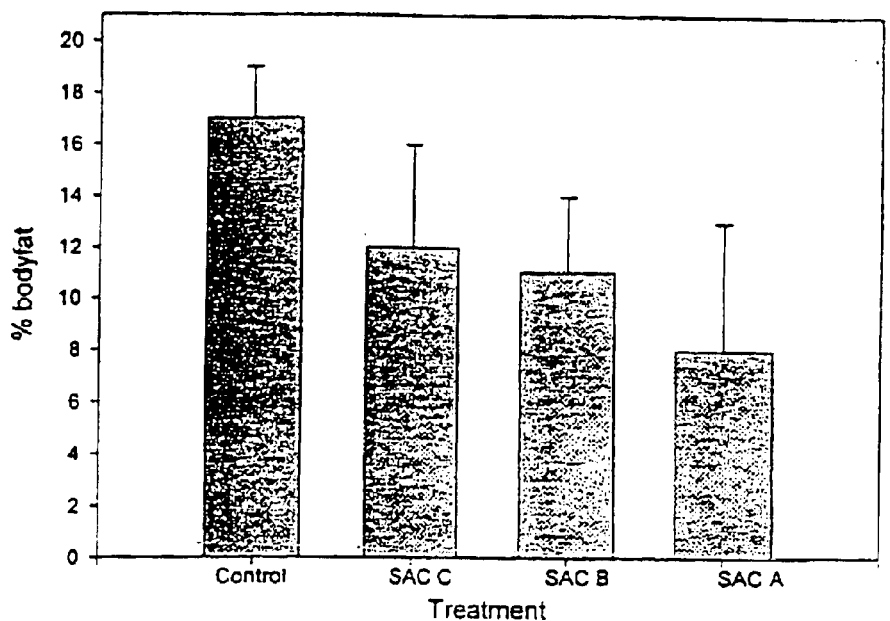
FIG. 21 is a bar graph which illustrates the effect of treatments on % bodyfat in poultry (mean and standard deviation presented).

Poultry treated with the experimental compounds showed a greater percentage of lean tissue than control counterparts. Bodyfat was 17+/−2, 12+/−4, 11+/−3 and 8+/−5 (mean and sd) respectively. FIG. 21 illustrates this.

EXPERIMENT 15

Effects of Nitric Oxide Donors on Anthelmintic Efficacy

Figure 22:
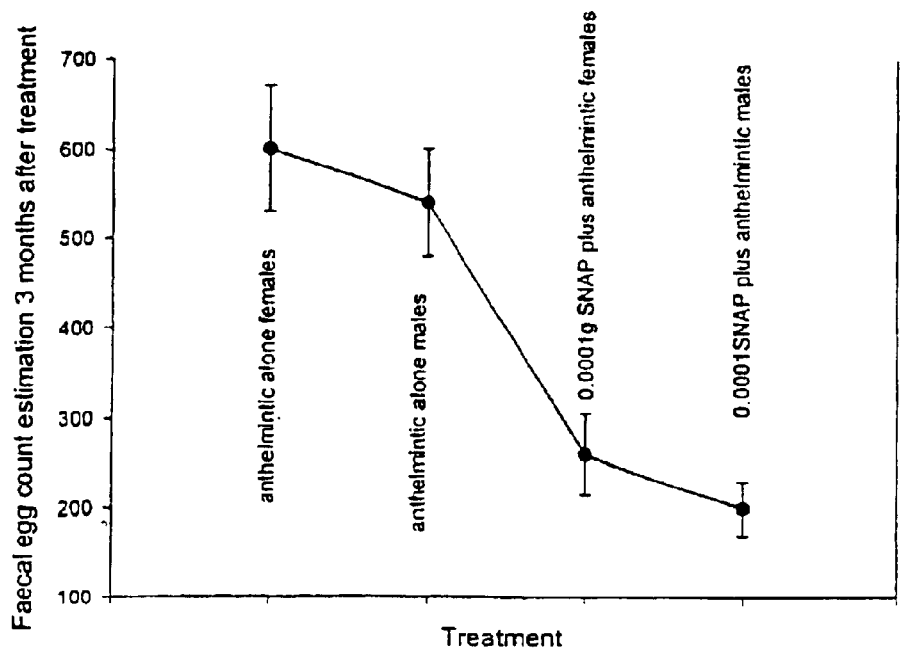
FIG. 22 is a line graph which illustrates effectiveness of a nitric oxide donor SNAP in increasing effectiveness of a standard anthelmintic. Mean and standard deviation displayed.

In a separate experiment 20 sheep (mixed male and females) received standard anthelmintic treatments similar to experiments 3 and 4, with anthelmintics and treatments given every four months. Treatment in 10 of these animals consisted of the anthelmintic dosing and S-nitroso-N-acetylpenicillamine, a nitric oxide donor at a dose of 0.0001 g per kg liveweight in an oral form. The other 10 received the anthelmintic and a glucose control. Anthelmintic successfulness in terms of time from treatment until faecal egg count rose to around 600 as described in experiments 3 and 4 was examined. Animals treated with the nitric oxide donor showed a better effectiveness of anthelmintic than control animals. FIG. 22 illustrates this.

It will be appreciated by those persons skilled in the art that the foregoing description is provided by way of example only and that the scope of the invention is not limited thereto.

What is claimed is:

1. A composition comprising a) at least one amino acid selected from the group consisting of valine, leucine, and isoleucine; b) the antistress agent metyrapone; and c) a further antistress agent selected from mifepristone, proglumide and astressin.

2. The composition according to claim 1 wherein the composition comprises valine, leucine, and isoleucine.

3. The composition according to claim 1 which further comprises vitamin C.

4. The composition according to claim 1 which further comprises a pyrrolopyrimidine or N-methylpyrrolidone.

5. The composition according to claim 1 which further comprises an antibiotic mannan oligosaccharide.

6. The composition according to claim 5 wherein the antibiotic is avilamycin.

7. The composition according to claim 1 which is encapsulated in a bolus or a time release capsule.

8. The composition according to claim 1 which further comprises a nitric oxide promoter selected from L-arginine diethylamine nitric oxide complex, sodium nitroprusside, and S-nitroso-N-acetylpenicillamine.

9. The composition according to claim 1 which further comprises a pharmaceutically or veterinarily acceptable diluent, excipient, carrier or solubiliser.

10. The composition of claim 1, wherein the composition is in the form of an animal feedstuff.

* * * * *